US008147501B2

(12) United States Patent
Waysbeyn et al.

(10) Patent No.: US 8,147,501 B2
(45) Date of Patent: Apr. 3, 2012

(54) ANASTOMOSIS METHOD

(75) Inventors: Igor Waysbeyn, Haifa (IL); Irina Vaysbeyn, Haifa (IL)

(73) Assignee: HDH Medical Ltd., Haifa (IL)

( * ) Notice: Subject to any disclaimer, the term of this patent is extended or adjusted under 35 U.S.C. 154(b) by 258 days.

(21) Appl. No.: 12/217,651

(22) Filed: Jul. 7, 2008

(65) Prior Publication Data

US 2009/0276035 A1 Nov. 5, 2009

(51) Int. Cl.
*A61F 11/00* (2006.01)
(52) U.S. Cl. ........................................... 606/108
(58) Field of Classification Search .................. 623/1.11, 623/1.13, 1.15, 1.23; 606/153, 144
See application file for complete search history.

(56) References Cited

U.S. PATENT DOCUMENTS

| | | | |
|---|---|---|---|
| 4,562,596 A | 1/1986 | Kornberg | |
| 4,787,899 A | 11/1988 | Lazarus | |
| 4,881,034 A * | 11/1989 | Kaufman et al. | 324/318 |
| 5,042,707 A | 8/1991 | Taheri | |
| 5,151,105 A * | 9/1992 | Kwan-Gett | 623/1.32 |
| 5,452,733 A | 9/1995 | Sterman et al. | |
| 5,695,504 A * | 12/1997 | Gifford et al. | 606/153 |
| 5,735,290 A | 4/1998 | Sterman et al. | |
| 5,800,521 A | 9/1998 | Orth | |
| 5,824,037 A * | 10/1998 | Fogarty et al. | 623/1.13 |
| 5,875,782 A | 3/1999 | Ferrari et al. | |
| 6,015,431 A | 1/2000 | Thornton et al. | |
| 6,036,699 A * | 3/2000 | Andreas et al. | 606/139 |
| 6,110,198 A | 8/2000 | Fogarty et al. | |
| 6,190,353 B1 * | 2/2001 | Makower et al. | 604/95.01 |
| 6,217,548 B1 | 4/2001 | Tsugita et al. | |
| 6,231,516 B1 * | 5/2001 | Keilman et al. | 600/485 |
| 6,264,611 B1 * | 7/2001 | Ishikawa et al. | 600/486 |
| 6,280,385 B1 * | 8/2001 | Melzer et al. | 600/423 |
| 6,280,466 B1 * | 8/2001 | Kugler et al. | 623/1.12 |
| 6,290,731 B1 | 9/2001 | Solovay et al. | |
| 6,344,038 B1 * | 2/2002 | Weber | 606/1 |
| 6,409,756 B1 | 6/2002 | Murphy | |
| 6,478,813 B1 * | 11/2002 | Keith et al. | 623/1.11 |
| 6,516,213 B1 * | 2/2003 | Nevo | 600/424 |
| 6,517,573 B1 * | 2/2003 | Pollock et al. | 623/1.15 |
| 6,524,335 B1 * | 2/2003 | Hartley et al. | 623/1.13 |
| 6,527,938 B2 * | 3/2003 | Bales et al. | 205/229 |
| 6,626,872 B1 * | 9/2003 | Navia et al. | 604/264 |
| 6,635,066 B2 | 10/2003 | Tanner et al. | |
| 6,689,152 B2 * | 2/2004 | Balceta et al. | 606/200 |
| 6,729,356 B1 | 5/2004 | Baker et al. | |

(Continued)

FOREIGN PATENT DOCUMENTS

WO    WO-95/12368    5/1995

(Continued)

OTHER PUBLICATIONS

In the U.S. Patent and Trademark Office, Office Action in re: U.S. Appl. No. 12/217,642, dated Oct. 7, 2011, 12 pages.

(Continued)

*Primary Examiner* — David Isabella
*Assistant Examiner* — Jonathan R Stroud
(74) *Attorney, Agent, or Firm* — Venable LLP; Michele V. Frank

(57) ABSTRACT

The present invention provides improved and simplified methods of vascular or hollow organ suture-less anastomosis for attachment of artificial standard vascular graft to the vessel wall in order to reduce the duration of the surgical procedure and its costs.

9 Claims, 21 Drawing Sheets

U.S. PATENT DOCUMENTS

| | | | |
|---|---|---|---|
| 6,743,173 B2* | 6/2004 | Penner et al. | 600/309 |
| 6,765,144 B1* | 7/2004 | Wang et al. | 174/36 |
| 7,329,279 B2* | 2/2008 | Haug et al. | 623/2.11 |
| 7,344,561 B2* | 3/2008 | DiCarlo | 623/1.34 |
| 7,785,365 B2* | 8/2010 | Holman et al. | 623/1.25 |
| 2001/0001114 A1* | 5/2001 | Tsugita et al. | 604/96.01 |
| 2001/0047153 A1 | 11/2001 | Trocki et al. | |
| 2002/0013569 A1* | 1/2002 | Sterman et al. | 604/508 |
| 2002/0058993 A1 | 5/2002 | Landau et al. | |
| 2002/0082554 A1 | 6/2002 | Lenarz et al. | |
| 2002/0091439 A1 | 7/2002 | Baker et al. | |
| 2002/0099394 A1 | 7/2002 | Houser et al. | |
| 2002/0173808 A1* | 11/2002 | Houser et al. | 606/153 |
| 2002/0183769 A1 | 12/2002 | Swanson et al. | |
| 2003/0019877 A1 | 1/2003 | Scarabelli et al. | |
| 2003/0033005 A1 | 2/2003 | Houser et al. | |
| 2003/0040792 A1 | 2/2003 | Gabbay | |
| 2003/0065341 A1* | 4/2003 | Schulze | 606/153 |
| 2003/0074007 A1 | 4/2003 | Rosengart | |
| 2003/0074055 A1 | 4/2003 | Haverkost | |
| 2003/0083679 A1 | 5/2003 | Grudem et al. | |
| 2003/0130671 A1* | 7/2003 | Duhaylongsod et al. | 606/153 |
| 2003/0130724 A1 | 7/2003 | DePalma et al. | |
| 2003/0158575 A1 | 8/2003 | Boylan et al. | |
| 2003/0158595 A1 | 8/2003 | Randall et al. | |
| 2003/0167087 A1 | 9/2003 | Piplani et al. | |
| 2003/0176877 A1 | 9/2003 | Narciso | |
| 2003/0179877 A1 | 9/2003 | Dezonno et al. | |
| 2003/0191518 A1* | 10/2003 | Spiridigliozzi et al. | 623/1.13 |
| 2003/0236567 A1 | 12/2003 | Elliot | |
| 2004/0082866 A1* | 4/2004 | Mott et al. | 600/486 |
| 2004/0106978 A1* | 6/2004 | Greenberg et al. | 623/1.13 |
| 2004/0158310 A1* | 8/2004 | Weber et al. | 623/1.15 |
| 2004/0193245 A1 | 9/2004 | Deem et al. | |
| 2004/0225213 A1* | 11/2004 | Wang et al. | 600/421 |
| 2004/0225351 A1 | 11/2004 | Weadock | |
| 2004/0230290 A1* | 11/2004 | Weber et al. | 623/1.15 |
| 2004/0236170 A1* | 11/2004 | Kim | 600/16 |
| 2005/0010277 A1* | 1/2005 | Chuter | 623/1.13 |
| 2005/0038502 A1* | 2/2005 | Waysbeyn et al. | 623/1.23 |
| 2005/0079132 A1* | 4/2005 | Wang et al. | 424/1.11 |
| 2005/0171599 A1 | 8/2005 | White | |
| 2006/0155313 A1* | 7/2006 | Yencho et al. | 606/153 |
| 2006/0280770 A1* | 12/2006 | Hossainy et al. | 424/423 |
| 2007/0027532 A1* | 2/2007 | Wang et al. | 623/1.44 |
| 2007/0112344 A1* | 5/2007 | Keilman | 606/41 |
| 2007/0123975 A1* | 5/2007 | Weber et al. | 623/1.16 |
| 2007/0156231 A1* | 7/2007 | Weber | 623/1.38 |
| 2007/0167955 A1* | 7/2007 | Arnault De La Menardiere et al. | 606/108 |
| 2007/0191816 A1* | 8/2007 | Behan et al. | 604/890.1 |
| 2009/0276032 A1 | 11/2009 | Waysbeyn et al. | |

FOREIGN PATENT DOCUMENTS

| | | |
|---|---|---|
| WO | WO-01/70091 | 9/2001 |
| WO | WO 02/17797 | 3/2002 |
| WO | WO-02/34164 | 5/2002 |
| WO | WO-03/053283 | 7/2003 |
| WO | WO-2004/045459 | 6/2004 |
| WO | WO 2005/013796 | 2/2005 |

OTHER PUBLICATIONS

U.S. Appl. No. 60/493,764, filed Aug. 11, 2003, Waysbeyn et al.

In the U.S. Patent and Trademark Office, Office Action in re: U.S. Appl. No. 12/217,642, dated Sep. 14, 2010, 10 pages.

In the U.S. Patent and Trademark Office, Final Office Action in re: U.S. Appl. No. 12/217,642, dated Mar. 7, 2011, 12 pages.

In the U.S. Patent and Trademark Office, Restriction/Election Requirement in re: U.S. Appl. No. 10/828,668, dated Feb. 14, 2007, 6 pages.

In the U.S. Patent and Trademark Office, Office Action in re: U.S. Appl. No. 10/828,668, dated May 7, 2007, 8 pages.

In the U.S. Patent and Trademark Office, Final Office Action in re: U.S. Appl. No. 10/828,668, dated Oct. 29, 2007, 11 pages.

In the U.S. Patent and Trademark Office, Office Action in re: U.S. Appl. No. 10/828,668, dated Dec. 15, 2008, 12 pages.

In the U.S. Patent and Trademark Office, Final Office Action in re: U.S. Appl. No. 10/828,668, dated Nov. 19, 2009, 10 pages.

* cited by examiner

ANASTOMOSIS METHOD

FIELD OF THE INVENTION

The present invention relates to methods for surgically performing anastomosis of hollow organs. More particularly, the present invention relates to methods of implanting an artificial graft in a target vessel.

BACKGROUND OF THE INVENTION

Aneurysms' ruptures of abdominal aorta are associated with particularly high mortality rates demanding urgent operative repair. Urgent and elective abdominal surgery results in substantial stress to the body, and especially in cases of ruptured aortic aneurysms, the mortality rate is extremely high. There is also considerable mortality and morbidity associated with elective open surgical intervention to repair aortic, thoracic and aorto-iliac aneurysms. For example, abdominal aneurysm intervention involves penetrating the abdominal wall to the location of the aneurysm to reinforce or replace the diseased section of the aorta. A prosthetic device, typically a synthetic tube graft, is used for this purpose. The graft serves to exclude the aneurysm from the circulatory system, thus relieving pressure and stress on the weakened section of the aorta at the aneurysm's location.

Repair of an aneurysms- and occlusions by surgical means is a major operative procedures. Substantial morbidity accompanies the aneurysm repair procedure, resulting in a protracted recovery period. Furthermore and as mentioned herein, the procedure entails a substantial risk of mortality. While surgical intervention may be indicated and the surgery carries attendant risk, certain patients may not be able to tolerate the stress of abdominal surgery. It is, therefore, desirable to reduce the mortality and morbidity associated with intra-abdominal surgical intervention.

Anastomosis is the surgical fusion of biological tissues, especially joining tubular organs to create an inter communication between them. Vascular surgery often involves producing an anastomosis between blood vessels or between a blood vessel and a vascular graft to create or restore a blood flow path to essential tissues. The first successful abdominal aortic aneurysm repair involving anastomosis creation was performed in 1951.

There are several known method of anastomosis:

One anastomosis method involves harvesting a vein in the body using an artificial conduit made of Dacron, PTFE, PU or other polymers tubing, and connecting the conduit as a bypass graft from a viable artery, such as the aorta, to the coronary artery downstream of the blockage or narrowing. A graft with both the proximal and the distal ends of the graft detached is known as a "free graft".

A second method involves rerouting a less essential artery, such as the internal mammary artery, from its native location so that it may be connected to the coronary artery downstream of the blockage. The proximal end of the graft vessel remains attached in its native position.

Until about a decade ago, essentially all vascular anastomosis were performed by conventional hand suturing. Suturing the anastomosis is a time-consuming and difficult task, requiring much skill and practice on the part of the surgeon. It is important that each anastomosis provides a smooth, open flow path for the blood and that the attachment be completely leaks-proof. A completely leak-proof seal is not always achieved on the very first try. Consequently, there is a frequent need for re-suturing the anastomosis to close any leaks that are detected. The time consuming nature of hand-sutured anastomosis is disadvantageous for several reasons. First, circulatory isolation and cardiac arrest are inherently very traumatic, and it has been found that the frequency of certain post-surgical complications varies directly with the duration for which the heart is under cardioplegic arrest (frequently referred to as the "cross-clamp time"). Secondly, because of the high cost of operating room time, any prolongation of the surgical procedure can significantly increase the cost of the bypass or other vascular operation to the hospital and to the patient. Thus, it is desirable to reduce the duration of the cross clamp time and of the entire surgery by expediting the anastomosis procedure without reducing the quality or effectiveness of the anastomosis.

The already high degree of manual skill required for conventional manually sutured anastomosis is even more demanding for closed-chest or port-access thoracoscopic bypass surgery. A newly developed surgical procedure designed to reduce the morbidity as compared to the standard open-chest procedure described in U.S. Pat. Nos. 5,452,733 and 5,735,290. In the closed-chest procedure, surgical access to the heart is made through narrow access ports made in the intercostal spaces of the patient's chest, and the procedure is performed under thoracoscopic observation. Because the patient's chest is not opened, the suturing of the anastomosis must be performed at some distance, using elongated instruments positioned through the access ports for approximating the tissues and for holding and manipulating the needles and sutures used to make the anastomosis. This requires even greater manual skill than the already difficult procedure of suturing anastomosis during open-chest surgery.

The biggest drawback of such an anastomosis is that it requires a fair amount of mobility of the two vessel ends to allow easy and accurate placement of the sutures, and it has a tendency to be constrictive.

In order to reduce the difficulty of creating the vascular anastomosis, there was a need to provide a rapid means for making a reliable anastomosis between a artificial graft or artery/vein and the aorta, native vessels of the heart or other blood vessels. A first approach to expediting and improving anastomosis procedures has been through stapling technology. Stapling technology has been successfully employed in many different areas of surgery for making tissue attachments faster and more reliably. The greatest progress in stapling technology has been in the area of gastrointestinal surgery. Various surgical stapling instruments have been developed for anastomosis of hollow or tubular organs, such as the bowel. These instruments, unfortunately, are not easily adaptable for use in creating vascular anastomosis. This is partially due to the difficulty in miniaturizing the instruments to make them suitable for using in smaller organs such as blood vessels. Possibly even more important is the necessity of providing a smooth, open flow path for the blood. Known gastrointestinal stapling instruments for anastomosis of tubular organs are designed to create an inverted anastomosis in which the tissue folds inward into the lumen of the organ that is being attached. This is acceptable in gastrointestinal surgery, where it is most important to approximate the outer layers of the intestinal tract. However, in vascular surgery, this geometry is unacceptable for several reasons. First, the inverted vessel walls would cause a disruption in the blood flow. This could cause decreased flow and ischemia downstream of the disruption, or, yet worse, the flow disruption or eddies could become a locus for thrombosis that could shed emboli or occlude the vessel at the anastomosis site.

Secondly, unlike the intestinal tract, the outer surfaces of the blood vessels will not grow together when approximated. The sutures, staples, or other joining device may therefore be needed permanently to maintain the structural integrity of the vascular anastomosis. Thirdly, to establish a permanent, non-thrombogenic vessel, the innermost layer should grow together for a continuous, uninterrupted lining of the entire vessel. Thus, it would be preferable to have a stapling instrument that would create vascular anastomosis that is everted, that is folded outward, or that creates direct edge-to-edge cooperation without inversion.

In recent years, methods have been developed in attempt to treat aneurysms without the attendant risks of intra-abdominal surgical intervention. For example, Komberg discloses in U.S. Pat. No. 4,562,596 "Aortic graft, device and method for performing an intraluminal abdominal aortic aneurysm repair" an aortic graft comprising a flexible tubular material having a plurality of struts along its body, to lend the graft stability and resiliency. The struts have angled hooks with barbs at their upper ends which are securely attached to the inside of the aorta above the aneurysm. Komberg's graft is inserted using a tubular device also disclosed in his patent. Komberg, however, only anchors the proximal end of the graft. Komberg claims that the downward flow of blood holds the distal graft securely in place, so that no mechanical attachment is necessary distally. The systolic blood pressure in the abdominal aorta, however, is typically in the magnitude of 120-200 mm of mercury (Hg). In spite of the direction of blood flow through the graft, proximal to distal, substantial back pressure within the aneurysm will result unless the distal end is also mechanically attached to the aorta in a manner that prevents substantial leakage of blood between the graft and the aorta. Without distal attachment, the Komberg's device will not effectively exclude the weakened arterial wall at the site of the aneurysm from the forces and stress associated with the blood pressure.

Another example can be seen in U.S. Pat. No. 4,787,899 "Intraluminal graft device, system and method", disclosed by Lazarus. Lazarus discloses a grafting system that employs a plurality of staples mounted in the proximal end of the graft. Lazarus's staples are forced through the aorta wall by means of a balloon catheter. Similarly to Komberg, Lazarus uses staples only in the proximal end of the graft. There is no teaching or suggestion as for mechanically attaching the graft to the distal aorta below the level of the aneurysm or occlusion.

Taheri discloses in U.S. Pat. No. 5,042,707 "Intravascular stapler and method of operating same" an articulatable stapler for implanting a graft in a blood vessel. The stapler is in the form of an elongated catheter with a plurality of segments mounted on the distal end of the catheter. The segments have beveled faces and are connected to each other by hinges. A wire runs through the catheter to the most distal segment, which is moved, in conjunction with the other segments, into a firing position that is substantially perpendicular to the main catheter body by the action of pulling the wire. The staple is implanted by using two other wires that act as fingers to bend the staple into its attachment position.

Taheri, however, appears to be a single-fire design that can only implant one staple at a time. After each staple is implanted, Taheri's design apparently requires that the catheter will be removed before another staple is loaded. In addition, Taheri does not suggest an appropriate density of staples to secure a graft against the pulsative blood flow of the aorta. Pressures within the aorta range from 120 mm Hg pressure to 200 mm Hg pressure. Without adequate attachment, the graft may leak around the edges continuing to allow life-threatening pressures to develop in the aneurysm. Moreover, the graft can even migrate.

Similar inherent defects as the ones referred herein are present in endovascular fastener and grafting apparatus that is disclosed in PCT application published as WO 02/17797. Moreover, it appears that some obstacles for blood flow in the vessel evolve from the wire ends. Other fasteners for the grafts are disclosed in American patent applications US 2003/0176877 by Narciso et al., US 2003/0130671 by Duhaylongsod et al and US 2003/0033005 by Houser et al.

All of the prior references exhibits a need for a sufficiently large section of healthy blood vessel tissue to ensure the reliable attachment of the prosthetic graft. The tissue above and below the aneurysm should be long enough for such attachment. The distal part of artery, close to iliac arteries, is usually long enough however the proximal part, called the aneurysm neck is not always long enough for attachment of the graft to the vessel wall.

There are number of shortcomings in the presently available graft products and their fixation within the aorta. Although sizing of "tube" or "bifurcated" grafts is radiographically usually assessed prior to surgery, it is necessary for the surgeon to have a large selection of graft lengths and diameters on hand to ensure an appropriate surgical outcome.

Additional shortcomings include the placement of a "circular" profile graft with an associated fixation device within an essentially "ovoid" profile vessel and the use of attachment means which fasten only to the insubstantial, structurally compromised (diseased) intima and media levels of the vessel wall.

Research has exposed yet another problem which indicates that the necks of the post-surgical aorta increase in size for approximately twelve months, regardless of whether the aneurysm experiences dimensional change. This phenomenon can result in perigraft leaks and graft migration.

Vascular endoprostheses (stent-grafts) are newly developed surgical device designed to reduce the drawbacks of suturing anastomosis procedure. The endo-luminal prosthesises were developed about 10 years ago to avoid major conventional open surgical repair for abdominal aortic aneurysm (AAA). Parodi in 1990 performed the first human stent graft implantation, backed by extensive animal experiments. In this method, incision is made in the patient groin and a catheter is inserted into a blood vessel that leads to the aorta. A stent graft (usually a Dacron tube inside a metal self expandable metal cylinder) is inserted through the catheter. Once the stent graft is in place, cylinder is expanded like a spring to hold tightly against the wall of the blood vessel. Stent graft can be supplied with the ancure device (EVT/ Guidant, ANCURE ENDO-HOOKS). The first production endografts to enter clinical trails in the US were approved by the FDA in September 1999 for clinical use under a careful monitored training program.

The treatment of AAA with stent grafts is rapidly evolving field. Several grafts models were introduced (U.S. Pat. Nos. 6,290,731, 6,409,756 are provided herein as references). The stent construction is unique for each type of device. Stents are working in very difficult conditions but there is no knowledge about the long-term durability. Analysis made by G. Riepe et al. (provided herein as references) shows that the long-term durability of conventional graft is still much higher then ones of stent graft.

Hence, although in recent years certain techniques have been developed that may reduce the stress, morbidity, and risk of mortality associated with surgical intervention to repair aortic aneurysms, none of the systems that have been developed effectively treats the aneurysm and excludes the affected section of aorta from the pressures and stresses associated with circulation. None of the devices disclosed in the references to this patent application provides a reliable and quick means to reinforce a diseased artery.

SUMMARY OF THE INVENTION

It is an object of the present invention to provide improved and simplified methods of vascular or hollow organ sutureless anastomosis for attachment of artificial standard vascular graft to the vessel wall in order to reduce the duration of the surgical procedure and its costs.

It is another object of the present invention to provide improved methods such attachment between an artificial standard vascular graft to the vessel wall using various delivery devices.

Therefore and in accordance with a preferred embodiment of the present invention, an anastomosis method for treating a blood vessel and other hollow organs having an aneurysm or occlusion edged by healthy portions: a proximal healthy portion and a distal healthy portion, said method comprising:
  providing a standard vascular graft having a length and a diameter corresponding the blood vessel/s or hollow organ to be treated, wherein said graft has a distal end/s and a proximal end and wherein said graft is provided with at least two docking heads that comprise a hollow truncated cone having a passage that is adapted to correspond an outer diameter of the graft and wherein said hollow truncated cone is provided with a plurality of outwardly pointing and inclined barbs, wherein a first docking heads is connected to said proximal end and at least second docking head is connected to said distal end;
  providing a delivery tool;
  stopping blood flow in the blood vessel;
  performing an incision and cleaning the aneurysm;
  inserting said proximal end to the proximal healthy portion manually or by a delivery tool;
  slightly pulling backwardly proximal end so as to dock said first docking head in the proximal healthy portion;
  inserting said distal end to the distal healthy portion manually or by a delivery tool;
  slightly pulling backwardly distal end so as to dock said at least one second docking head in the distal healthy portion;
  restoring the blood flow;
  suturing the incision.

Furthermore, in accordance with another preferred embodiment of the present invention, the method further comprising:
  providing at least one docking head that is adapted to move along said graft;
  adapting a length of said vascular device to the length of the blood vessel to be treated by moving said at least one docking head along said graft;
  fixing said at least one docking head on said graft in a suitable position;

Furthermore, in accordance with another preferred embodiment of the present invention, said delivery tool is a tubular catheter having a sharp tip that is adapted to be concealed, a wire adapted to be removed, and an inflatable balloon at its proximal end, wherein said method further comprising:
  perforating a blood vessel/hollow organ wall by said sharp tip;
  concealing said sharp tip;
  advancing said tubular catheter to the proximal healthy portion;
  inflate said balloon so as to fix said tubular catheter in the proximal healthy portion and stop the blood flow;
  removing said wire;
  mounting said graft over said tubular catheter;
  guiding said proximal end to the proximal healthy portion;
  deflating said balloon and removing said tubular catheter through said graft.

Furthermore, in accordance with another preferred embodiment of the present invention, said delivery tool is forceps.

Furthermore, in accordance with another preferred embodiment of the present invention, said forceps is provided with elongated and curved jaws that can be inserted within said graft and wherein a rounded protrusion is provided at a guiding end of said elongated and curved jaws.

Additionally, in accordance with another preferred embodiment of the present invention, said forceps are provided with jaws adapted to be positioned in a gap between said truncated cone and said graft so as to guide said distal end or said proximal end to the vessel healthy portion.

BRIEF DESCRIPTION OF THE FIGURES

In order to better understand the present invention and appreciate its practical applications, the following Figures are attached and references herein. Like components are denoted by like reference numerals.

It should be noted that the figures are given as examples and preferred embodiments only and in no way limit the scope of the present invention as defined in the appending Description and Claims.

DETAILED DESCRIPTION OF THE INVENTION AND THE FIGURES

The present invention provides new and unique methods of cardiovascular graft implantation in hollow organs, especially in blood vessels for treating aneurysm. The new methods enable attaching the graft to the host vessel without the need to suture it; thus treating anastomosis in a relatively rapid manner. The suture-less anastomosis is performed in the distal side as well as in the proximal side of the aneurysm so as to accomplish the anastomosis with minimal loss of blood.

According to the anastomosis method provided herein, the graft is prepared to a required size, blood flow is stopped for relatively short while in the sick vessel, aneurysm incision and clearing is performed and the graft is introduced and installed in the aneurysm. The non-suture ends connection of the graft to the vessel provides leak proof sealing of the connections and rapid blood supply restoration.

The graft is being prepared to fit the required size according to the patient's vessel dimensions. This is performed prior to the operation. In some of the embodiments disclosed here, modular parts are provided so as to facilitate the leak-proof connection between the graft and the vessel.

In a preferred aspect of the present invention a vascular device is provided for treating a blood vessel with aneurysm. The vascular device comprises a graft, which can be a tubular or bifurcated graft, having a proximal portion and a distal portion. A first docking head is provided at the proximal portion and a second docking head is provided at the distal portion. If the graft is a bifurcated one, both ends of the distal portion are provided with the docking heads. The vascular device is coupled to the blood vessel on both sides of the aneurysm so as to replace this portion of the blood vessel by the first docking head and the second docking head. The docking heads act as guiding, anchoring and sealing means in a suture-less and rapid manner.

In another preferred aspect of the present invention, the graft that is prepared prior to the opening of the aneurysm area is longer than the sick vessel portion itself and the docking head that is provided at an end of the graft is mounted so as to allow movement of the docking head along the end portion of the graft. During the anastomosis, the surgeon can adjust the docking head or at least one of the docking heads and fasten it or them at the ends of the graft in the required place according to the situation that is revealed after actual opening of the aneurysm. The docking head can be fastened by any of the conventional means such as a fit, glue, suture, clips, staples. Any other technique for attaching the docking head in the required place on the graft is covered by the scope of the present invention.

Figure 1:
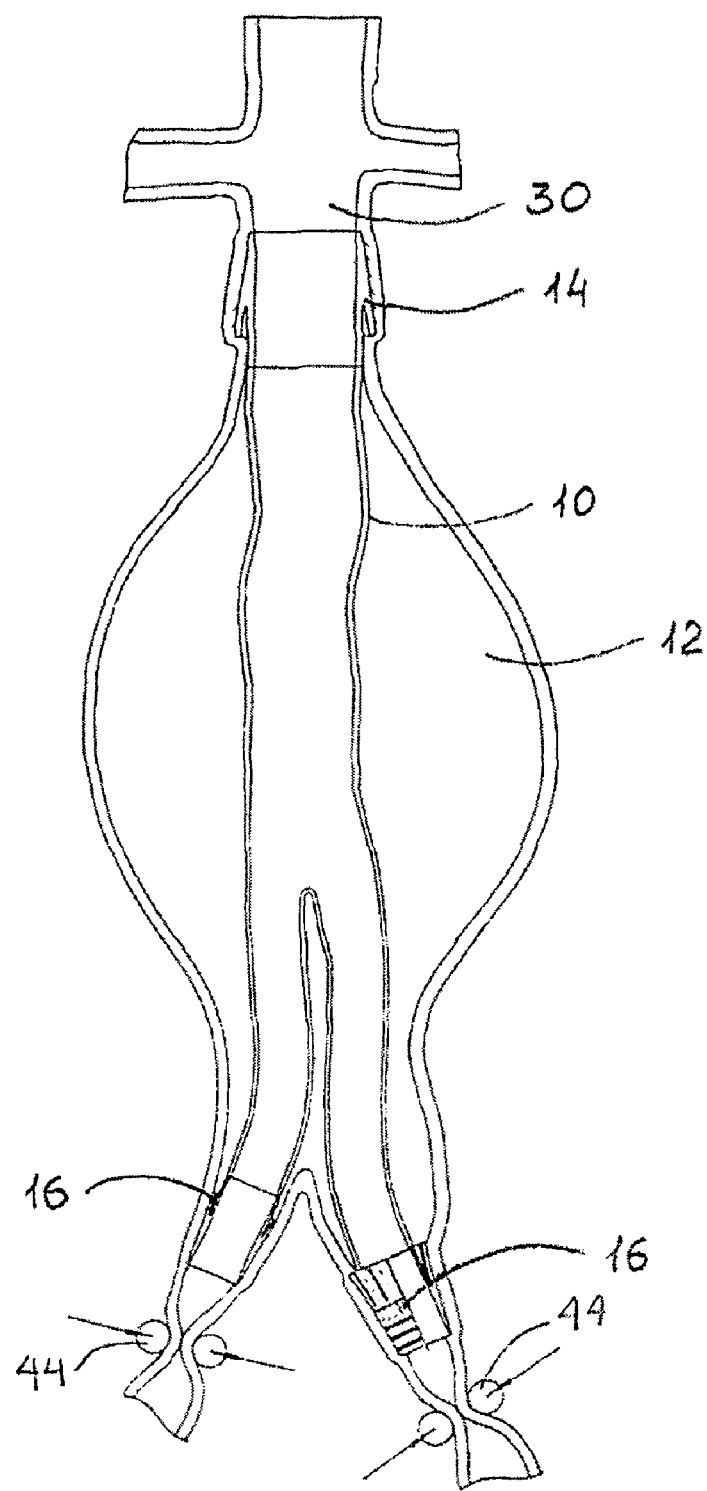
FIG. 1 illustrates a cross sectional view of a bifurcated graft in accordance with a preferred embodiment of the present invention, inserted within an aortic aneurysm.

Reference is now made to FIG. 1 illustrating a cross sectional view of a bifurcated graft in accordance with a preferred embodiment of the present invention, inserted within an aortic aneurysm. A bifurcated graft 10 is inserted within an aneurysm 12 in a blood vessel. Three ends of bifurcated graft 10 are provided with concentric docking heads, a first docking head 14 at the proximal end and two docking heads 16 at the distal ends of the graft. Docking heads 14 and 16 are adapted to couple the graft to the vessel without suturing it and provides the surgeon with the ability to rapidly connect the graft to the aneurysm. The docking head according to the present invention has three functions: guiding the graft into the vessel, anchoring it into the inner wall of the vessel and sealing it so as to provide a continuous wall that prevents blood from leaking out of the vessel. The procedure of inserting the graft in the aneurysm is explained herein after.

Figure 2:
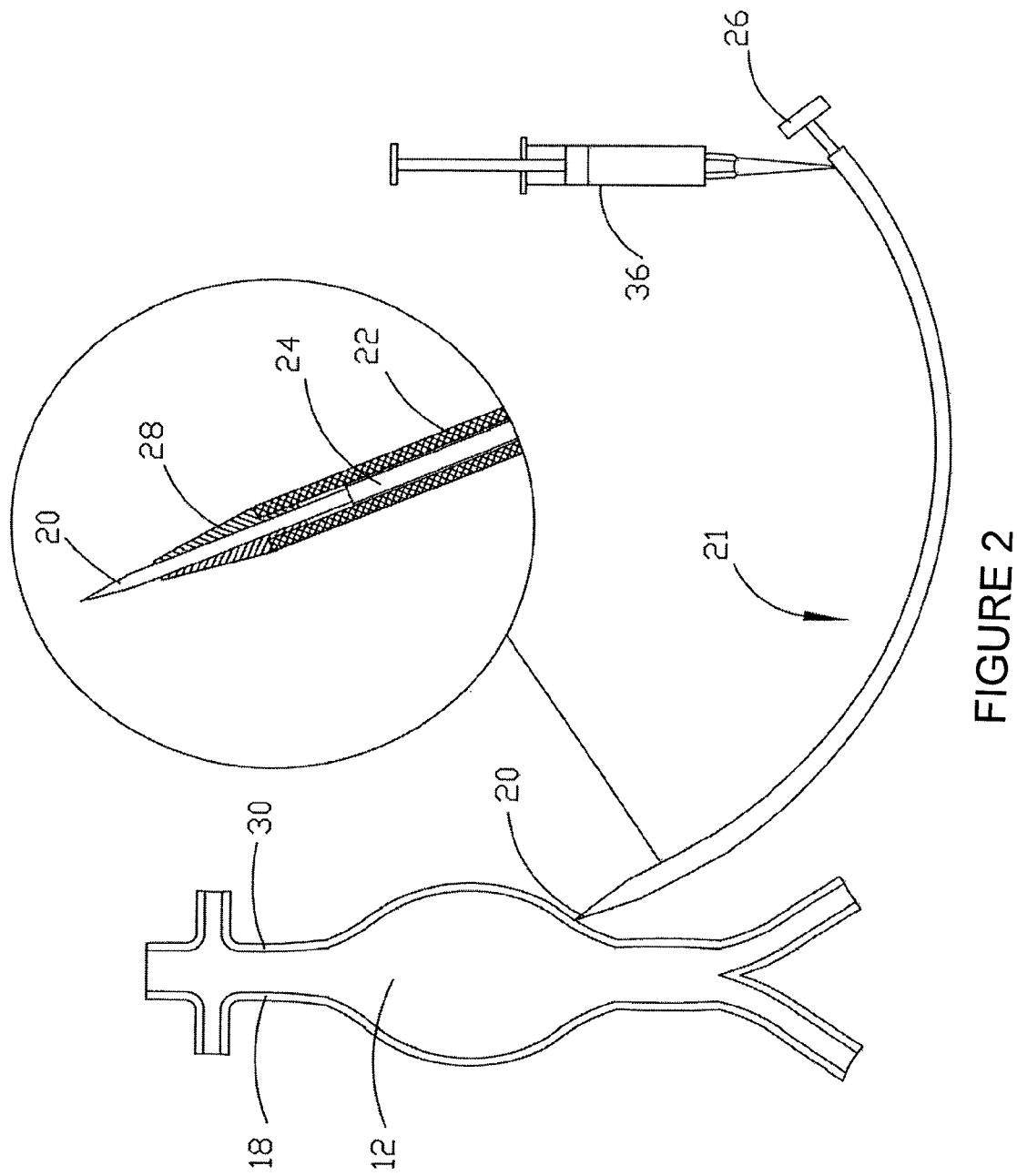
FIGS. 2-3 illustrate the procedure of opening an access to the aneurysm by a catheter in accordance with a preferred embodiment of the present invention.
Figure 3:
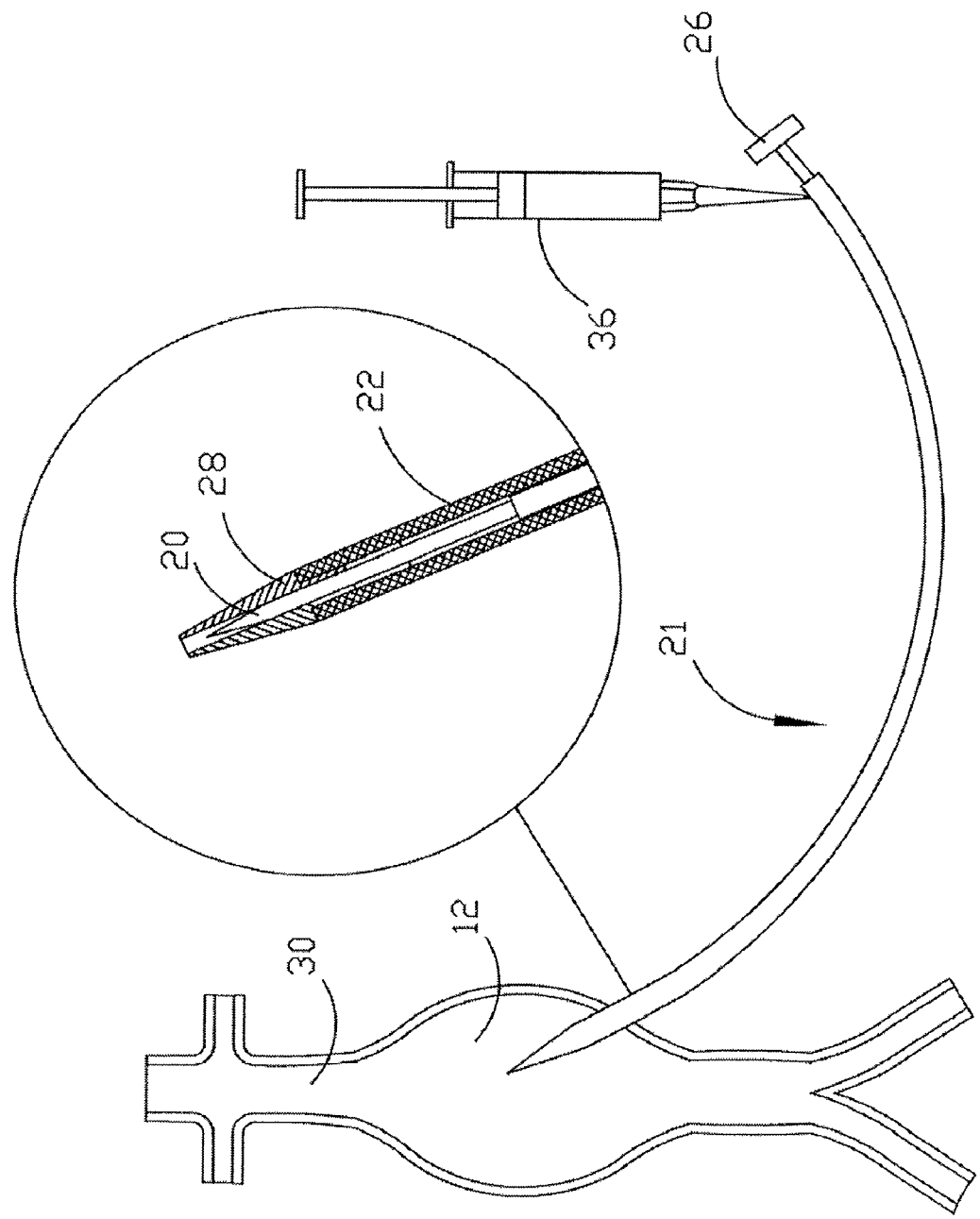
Figure 4:
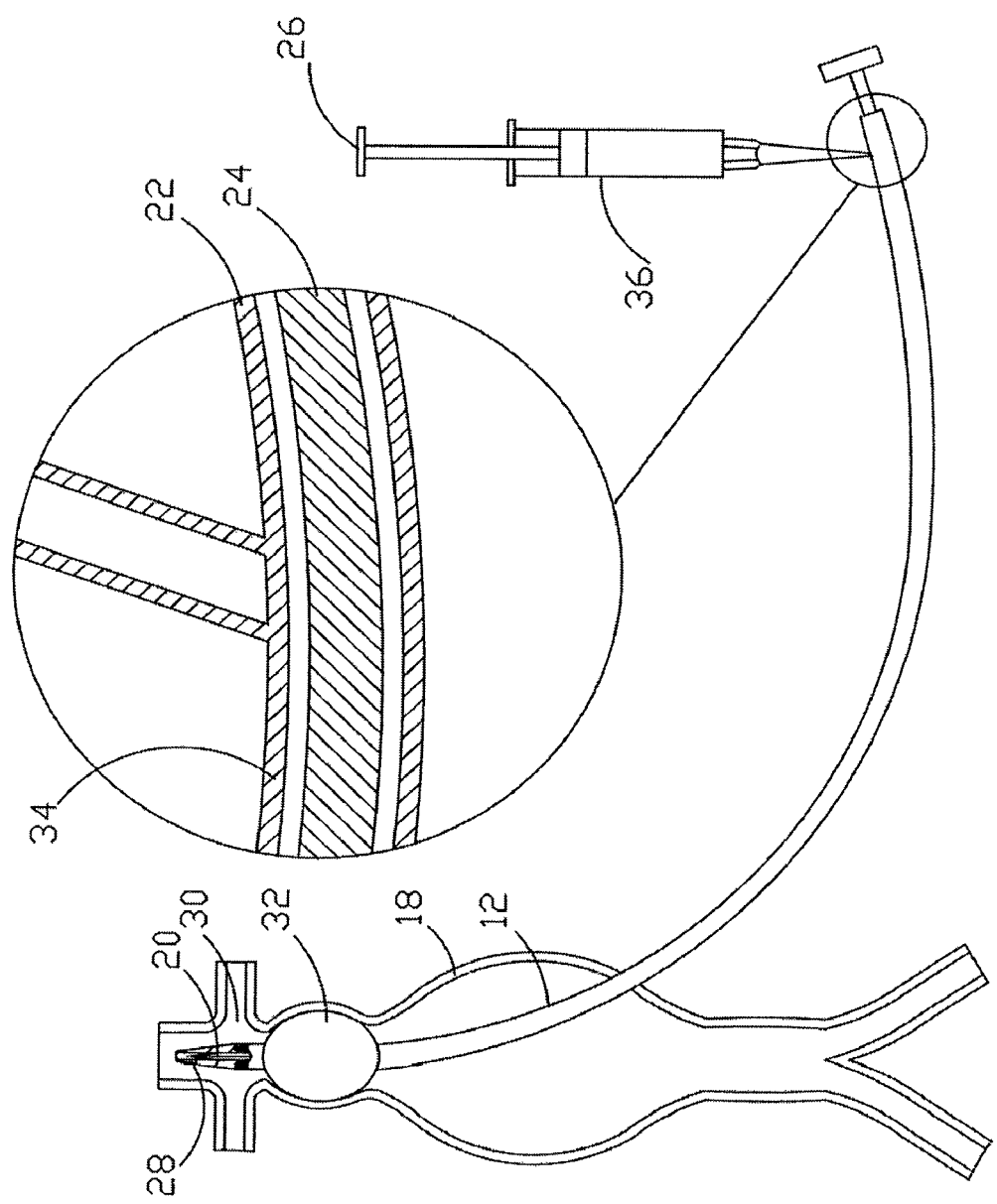
FIG. 4 illustrates the delivery catheter fixed on top of the aneurysm, ready for insertion of the proximal side of a graft in accordance with a preferred embodiment of the present invention.

Reference is now made to FIGS. 2-4 illustrating the procedure of opening an access to the aneurysm by a delivery catheter in accordance with a preferred embodiment of the present invention. FIG. 2 illustrates a delivery catheter 21 that is basically a catheter tube 22 provided with a sharp tip 20 (sharp tip 20 is shown in an enlarged view and act as a stylet) that is used to puncture a wall 18 of aneurysm 12 and enter within the vessel. Sharp tip 20 is connected to a wire 24 that passes through catheter tube 22 and facilitates in its insertion. Sharp tip 20 is provided with a withdrawal means 26 at its distal end. As shown in FIG. 3, after the proximal side of catheter tube 22 is within aneurysm 12, sharp tip 20 is slightly withdrawn into the catheter's body. Sleeve 28 (can be seen clearly in the enlargements in FIGS. 2 and 3) receives sharp tip 20 so that no additional puncturing is performed once the catheter's proximal side is within the vessel. Catheter tube 22 is pushed further into the vessel so that its proximal side resides within the healthy neck portion of the vessel 30. As shown in FIG. 4, after positioning the proximal side of delivery catheter 21 within neck 30, a laterally inflatable balloon 32 that is provided in the proximal portion of the catheter is inflated so as to establish a firm hold of catheter tube 22 in neck 30. The surface of inflated balloon 32 is covered with an antifrictional structure which is not cooperating with blood. Delivery catheter 21 is provided with a special tube 34 that extends from its distal side (shown in the enlargement in the Figure) to the balloon in its proximal side wherein liquid can be inserted by a syringe 36 into tube 34 so as to inflate balloon 32. Catheter tube 22 provided with wire 24 is used to guide the graft into the right positioning in the aneurysm's proximal neck. After the catheter is firmly installed within the neck of the vessel and in accordance with a preferred embodiment of the present invention, the graft can be guided onto the delivery catheter and into the aneurysm.

Figure 21:
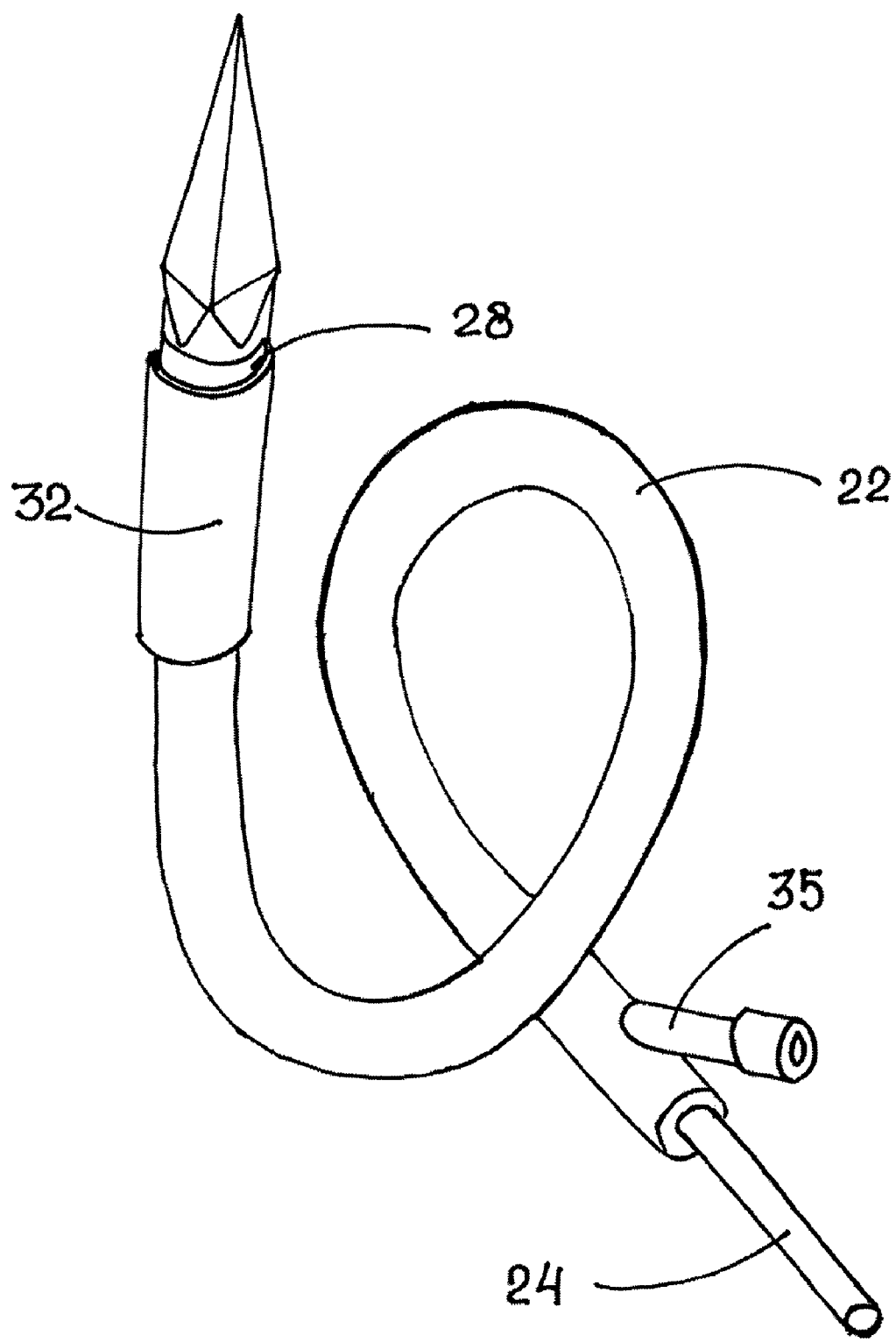
FIG. 21 illustrates a perspective view of a delivery catheter for facilitating the insertion of a graft in accordance with a preferred embodiment of the present invention.

Reference is now made to FIG. 21 illustrating a perspective view of a delivery catheter for facilitating the insertion of a graft in accordance with a preferred embodiment of the present invention. Catheter tube 22 is provided with sharp tip 20 that is adapted to puncture the aneurysm as shown herein before so as to enter into the vessel. Sharp tip 20 is connected to the proximal end of the catheter through a wire 24 that partially protrudes from the proximal side of the catheter and its end act also as withdrawal means 26 to withdraw sharp tip 20 to within sleeve 28. Wire 24 is adapted to maintain catheter tube 22 stiff when it is inserted countercurrent to the blood flow and into the proximal neck of the vessel. After the balloon is inflated in the neck as explained herein before, wire 24 can be fully removed through the catheter's distal end using withdrawal means 26. The delivery catheter is provided with a side extension 35 adapted to deliver liquid from a syringe (not shown in FIG. 21, shown in FIGS. 2-5) that is connected to the extension through a tubing so as to inflate a balloon (shown in FIG. 21 in an un-inflated position). When wire 24 is withdrawn from catheter tube 22, the catheter is fully flexible.

It should be noted that the delivery catheter as disclosed in the present invention is adapted to stop the blood flow through the aneurysm's proximal neck when the installation of the graft is performed. In prior art procedures, the length of the neck is crucial in determining whether to do the procedure or not, and a relatively short neck between the aneurysm and the renal arteries will result in avoiding the procedure all together since there is no possibility to perform such a long procedure while preventing blood from flowing into the renal arteries. In the procedure disclosed herein, the proximal portion of the delivery catheter is pushed into the neck and the balloon that is provided in the proximal portion can be inflated also in a relatively short neck. Moreover, the balloon can be also inflated in the area of the renal arteries connection or even above them so that the blood to the kidneys is stopped. Since the procedure of graft implantation in accordance with the present invention is rapid, the blood flow to the kidneys can be stopped for that short while. Therefore, even an aneurysm having a relatively short proximal neck can be treated (FIG. 5 illustrates a case in which the blood flow to the renal arteries is being blocked).

Figure 5:
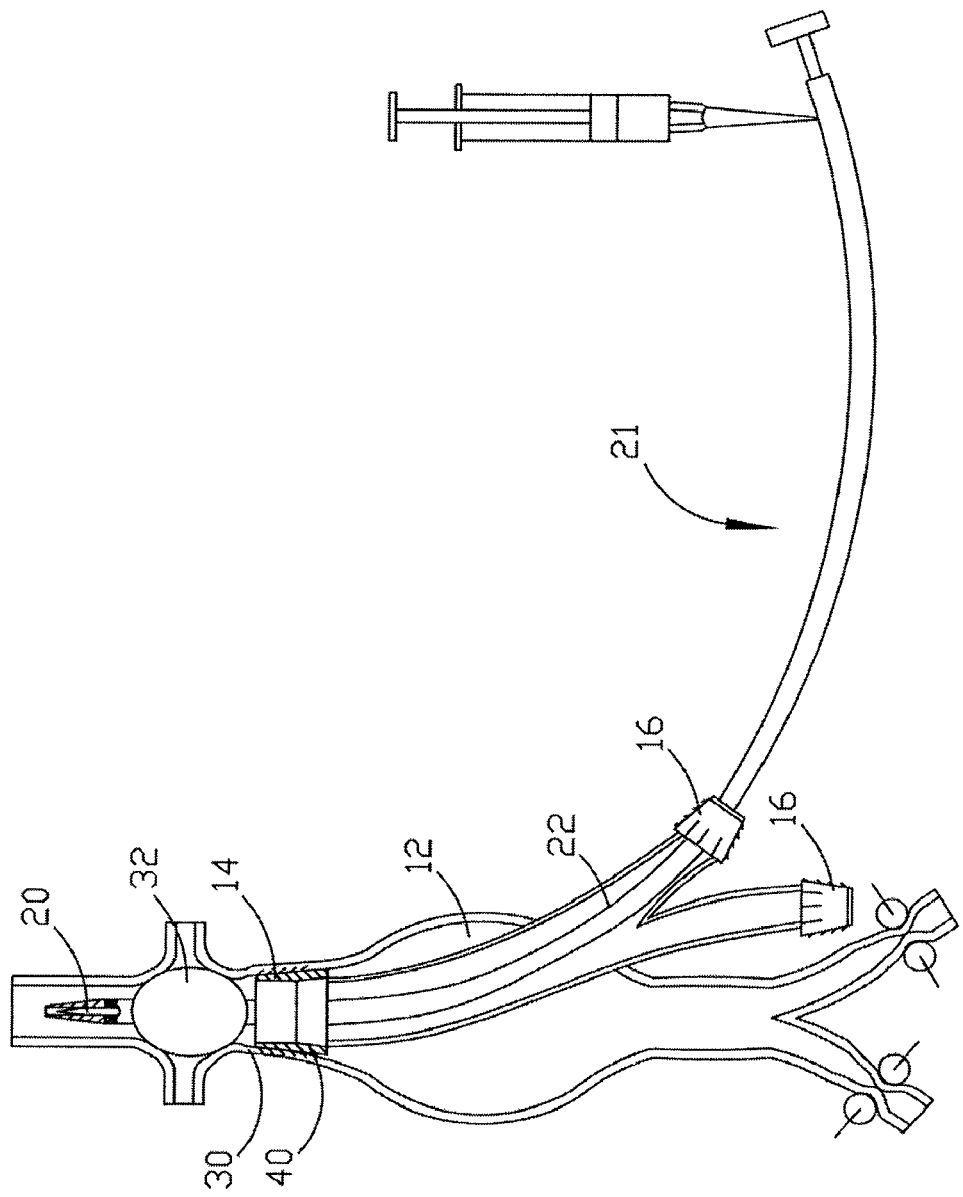
FIG. 5 illustrates a cross sectional view of the bifurcated graft shown in FIG. 1, inserted in a proximal neck of the aneurysm in the vessel along the catheter shown in FIGS. 2-4.
Figure 6:
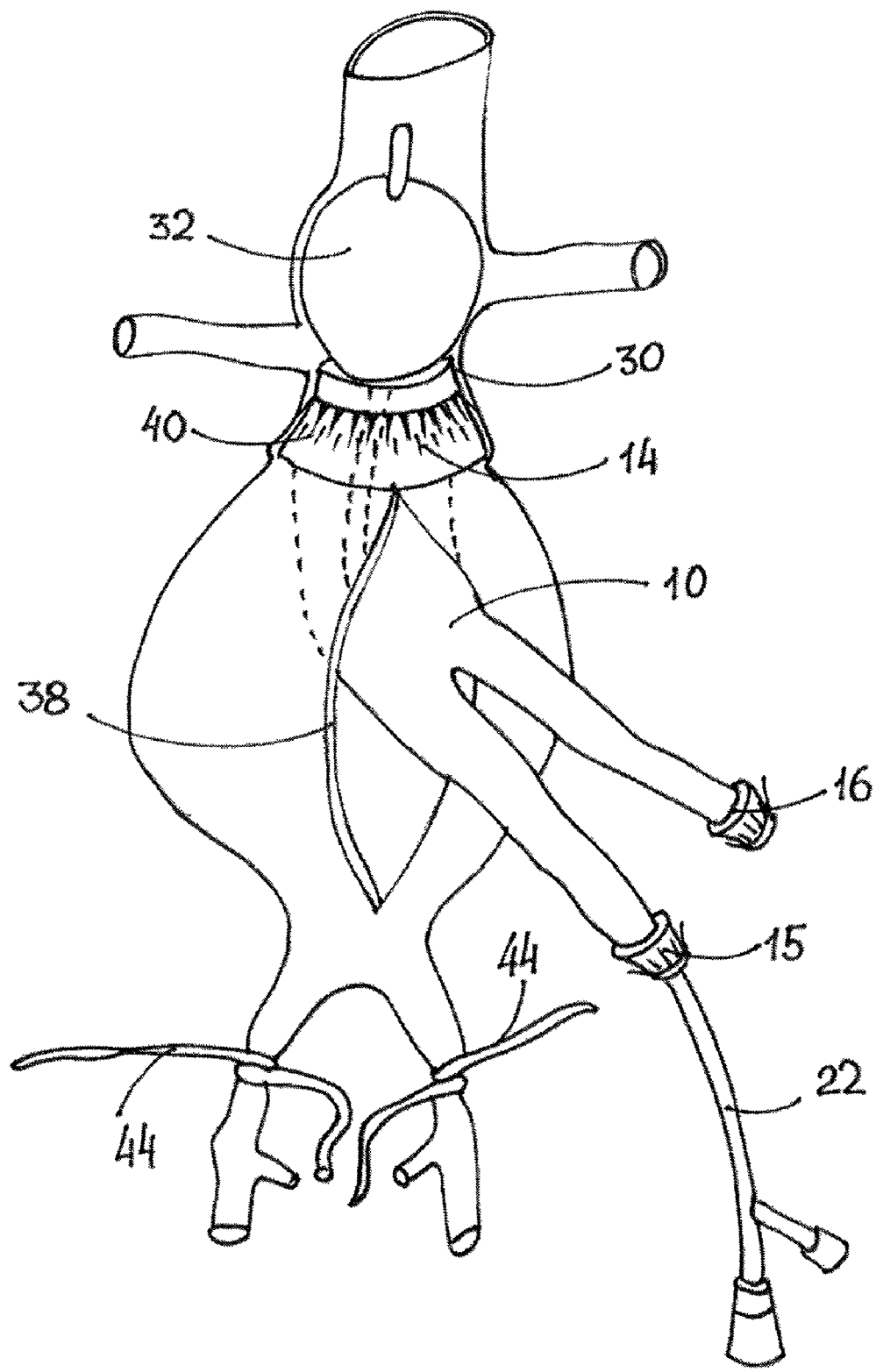
FIG. 6 illustrates a perspective view of the bifurcated graft shown in FIG. 1, passing over catheter tube up to its proximal end.

Reference is now made to FIGS. 5 and 6 illustrating a cross sectional view and a perspective view of the bifurcated graft shown in FIG. 1, inserted in a proximal end of an aneurysm in the vessel along with a catheter. Since balloon 32 stops the blood from flowing towards aneurysm 12, the vessel can be now cut without loose of blood and in order to guide the graft onto catheter tube 22. Bifurcated graft 10 is guided over catheter tube 22 while the proximal side of the graft 10 is inserted into healthy vessel neck 30 for docking. As mentioned herein before, docking the graft into the neck of the vessel using a docking head eliminates the need to suture the graft to the vessel as performed in prior art procedures. The docking procedure is relatively rapid.

In order to firmly and sealingly couple the graft to the vessel, docking head 14 is inserted into neck 30. The types of docking head will be comprehensively explained herein after, however, basically, docking heads 14 and 16 are conical structures provided with a plurality of inclined barbs 40. Inclined barbs 40 are arranged at the circumference of the conical structure in at least one row and are distally pointed to the direction of the graft's body. The conical structure followed by the graft is inserted into neck 30 through its narrow end while inclined barbs 40 smoothly pass through a portion of the neck. Then, docking head 14 is being slightly pulled back. Upon pulling back the conical structure, inclined barbs 40 are being imbedded within the neck, forming a firm and sealed connection between the vessel and the graft. The mechanism used in order to anchor the graft in the vessel's inner wall is similar to the mechanism of a bee's sting. Pulling docking head 14 backwardly replaces the time consuming suturing procedure that takes place in the prior art grafting.

Figure 19:
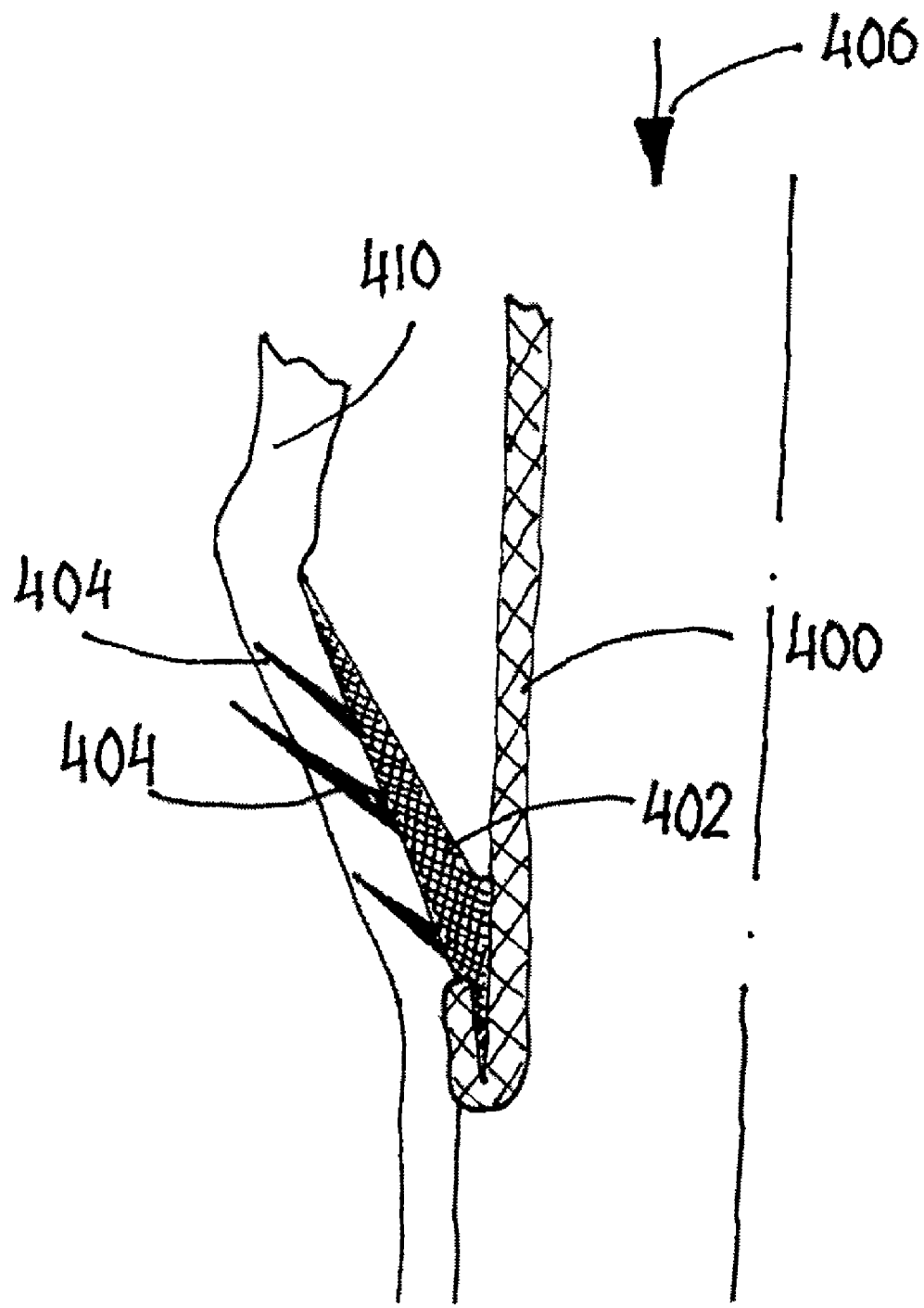
FIG. 19 illustrates an enlarged view of a docking head in accordance with a preferred embodiment of the present invention, nailed to the vessel.
Figure 20:
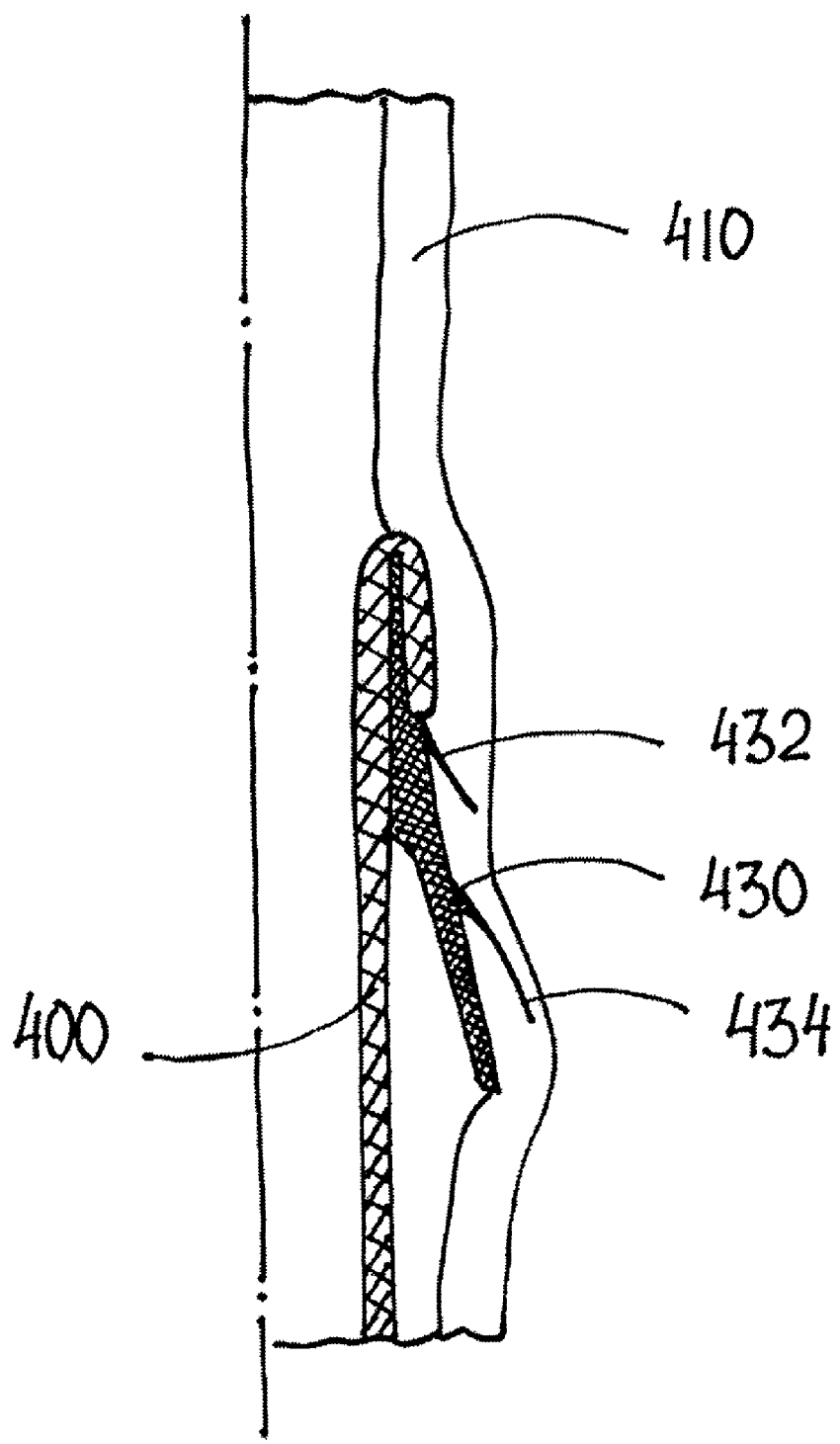
FIG. 20 illustrates an enlarged view of a docking head in accordance with another preferred embodiment of the present invention.

Reference is now made to FIG. 19 and FIG. 20 illustrating an enlarged view of docking heads in accordance with preferred embodiments of the present invention, nailed to the vessel's inner wall. In FIG. 19, graft 400 is provided with a docking head 402, adapted to connect the graft to the circumference of a vessel 410. Barbs 404 are pointed backward; opposite the direction to which graft 400 is pushed (this direction is marked by arrow 406). The barbs can be concaved relative to the profile of the graft, convex or partially convex and partially concaved so that they can be nailed into the blood vessel wall. Those shapes of the barbs prevent them from contiguously bend on the graft's wall without sticking into the blood vessel's wall. After positioning of the graft, graft 400 is pulled slightly backwardly so as to nail barbs 404 into vessel 410. In FIG. 20, graft 400 is provided with docking head 430 that has a concaved profile that facilitates its insertion into vessel 410. Docking head 430 is provided with barbs that are connected to the docking head in different positions. Barb 432 is connected in a concaved orientation while barb 434 is connected in a convex orientation. Different types of barbs orientations provide a firm coupling between vessel 410 and docking means 430 so as to sealingly block any blood leakage from the vessel. The orientations of the barbs also provide firm anchoring of the graft within the vessel so that there will be substantially no relative movement between the two.

Figure 7:
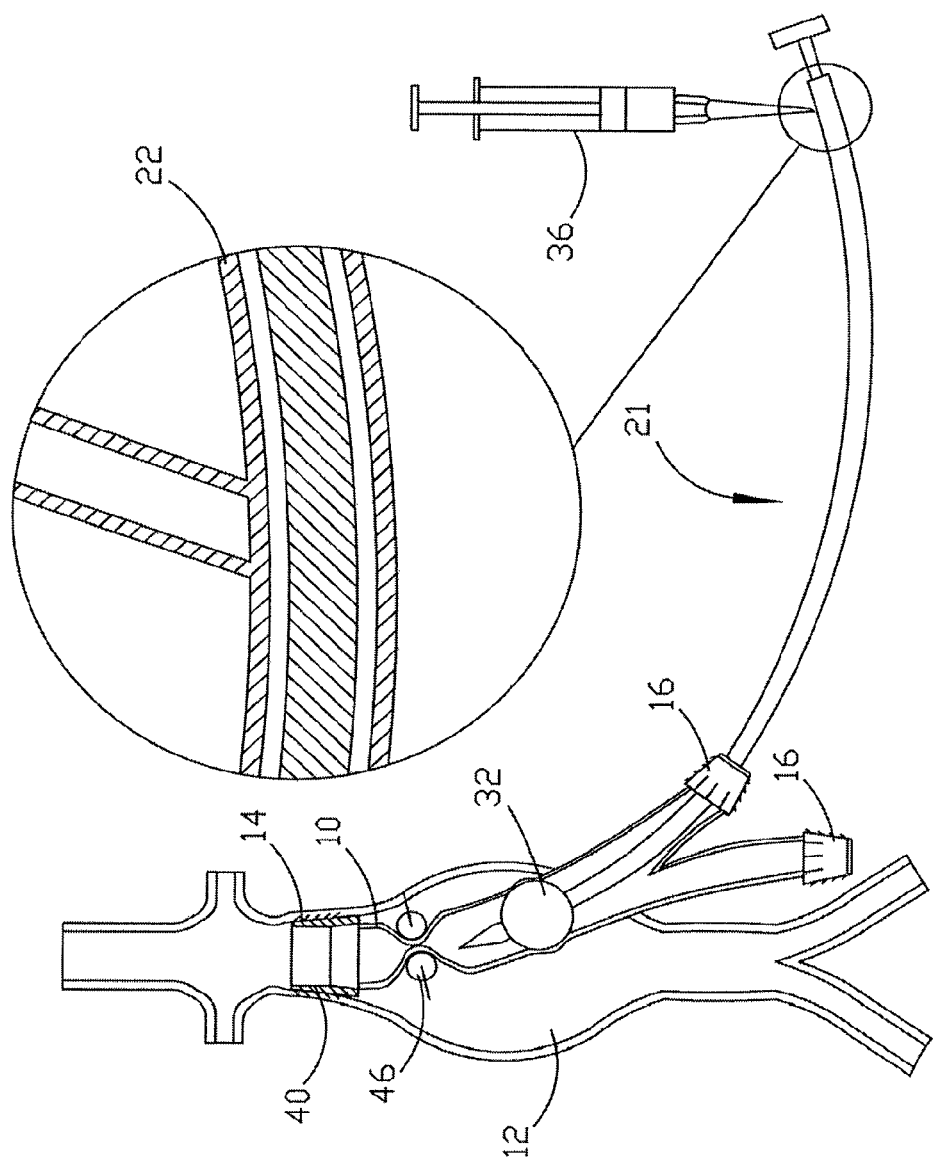
FIG. 7 illustrates a cross sectional view of the graft shown in FIG. 1 in an advanced stage of catheter removal in accordance with a preferred embodiment of the present invention.

Reference is now made to FIG. 7 illustrating a cross sectional view of the graft shown in FIG. 1 in an advanced stage of graft insertion in accordance with a preferred embodiment of the present invention. At this point, delivery catheter 21 is being removed. Balloon 32 is being slightly deflated so as to the accord the graft diameter and is being withdrawn towards the proximal portion of the graft. The removal of delivery catheter 21 allows blood to flow into the graft. In order to prevent blood loose, clip 46 is clamped on graft 10 in an area from which delivery catheter 21 had been already removed. At this point, delivery catheter 21 is being completely withdrawn from within the graft. The fact that a proximal clip is removed in this stage to the graft itself is very significant especially in cases in which the proximal healthy neck is relatively short and the renal arteries are being blocked. As mentioned herein before, in cases the healthy neck is relatively short and there is a need to block the renal arteries for the procedure, the whole procedure is being relinquished since the damage to the kidneys may be beyond repair. Due to the devices and the methods of the present invention, the blockage of blood to the kidneys is for a very short time and there is almost no risk involved in the procedure. The blood flow to the kidneys is restored before the distal docking is performed.

Reference is being made again to FIG. 1 illustrating a cross sectional view of the bifurcated graft in accordance with a preferred embodiment of the present invention, inserted within an aortic aneurysm. Bifurcated graft 10 is connected in the proximal side to the vessel's neck 30 and is now ready to be connected in its distal side to the two vessels that bifurcate from aneurysm 12. As mentioned herein before, graft 10 bifurcates into two portions in its distal side. Both portions are being connected to both vessels in the same way as the connection of the graft to the proximal neck. For that, each bifurcation is provided with docking head 16 that is basically similar to docking head 14 and is also provided with elastic barbs that are directed towards the graft itself. The connection is immediate and simple while graft 10 is positioned so as to allow docking head to be placed in the healthy distal vessels. Docking heads 16 are pushed into the vessels and than slightly pulled outwardly so that the elastic barbs are nailed into the vessel and sealingly and firmly connect bifurcated graft 10 to the vessels. Just before the actual connection of the distal sides to the vessel, clip 46 (not shown in FIG. 1) is removed so as to establish a flow of blood through the graft. After the connection is complete, clips 44 can be removed so as to establish a blood flow to the blocked areas.

It is important to emphasis again that since the new procedure is a rapid one due to the use of docking heads instead of suturing, the blockage of blood to the areas that receive blood through the treated vessel is for relatively short while. One of the features that may have lethal consequences of any procedure in which aneurysm is treated is the blockage of blood flow through this vessel during the whole operation. One of the major faults of the prior art procedures is the fact that the connection of the graft to the vessel is extremely time consuming, even for a very experienced surgeon. Using the procedures and grafts provided in the present invention markedly reduces the time of operation so that the blood is blocked just to a minimum time necessary to dock the graft in the vessel.

Figure 8:
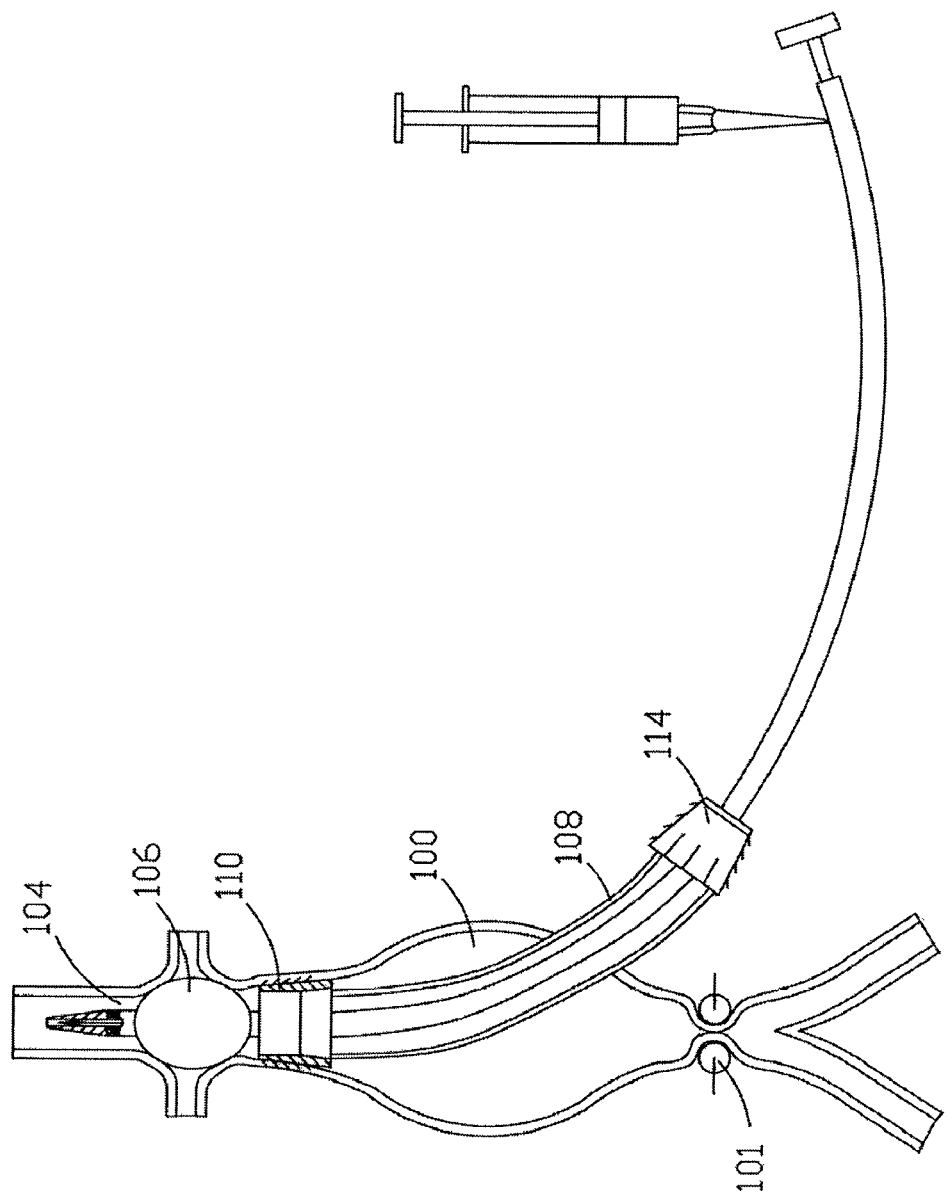
FIGS. 8-13 illustrate stages of a tube graft installation in a vessel with aneurysm in accordance with other preferred embodiments of the present invention.
Figure 9:
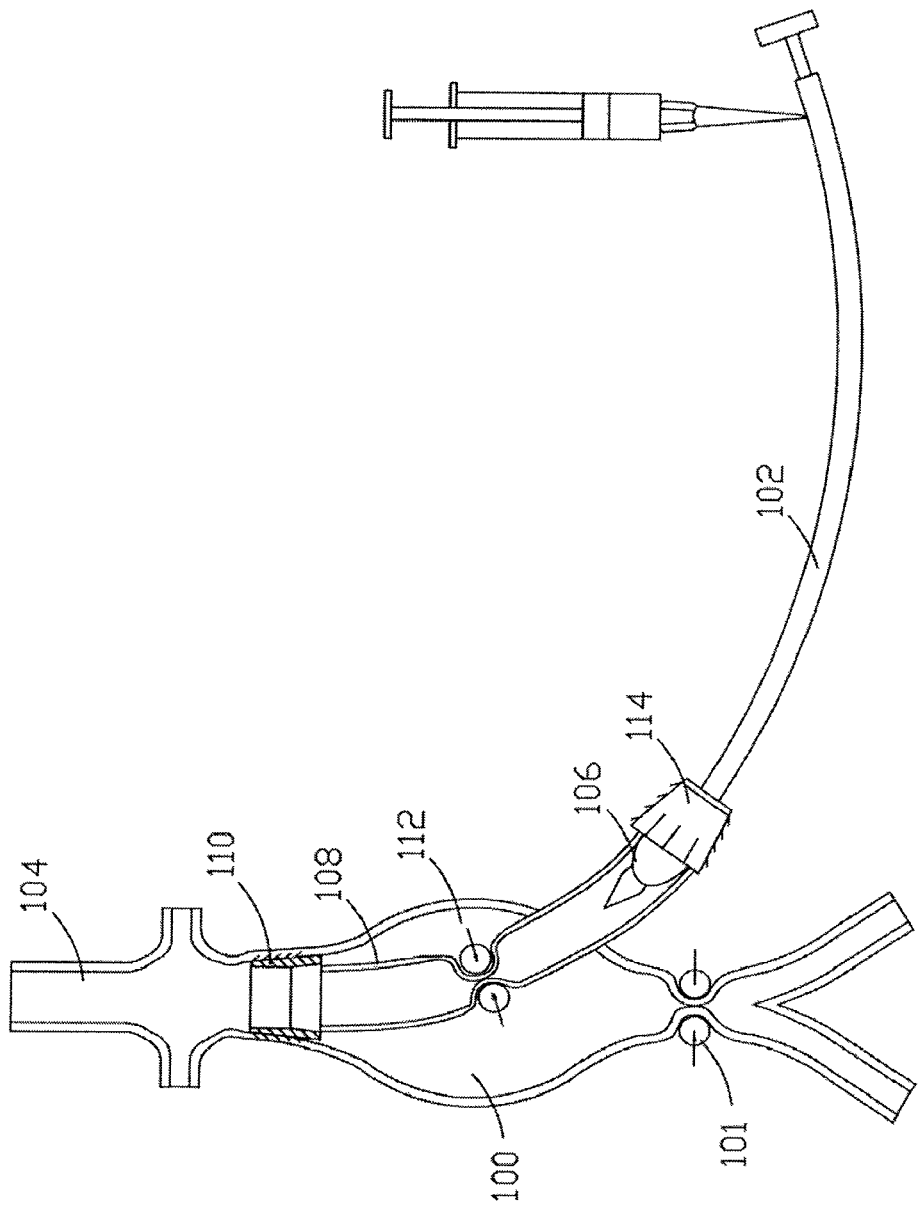
Figure 10:
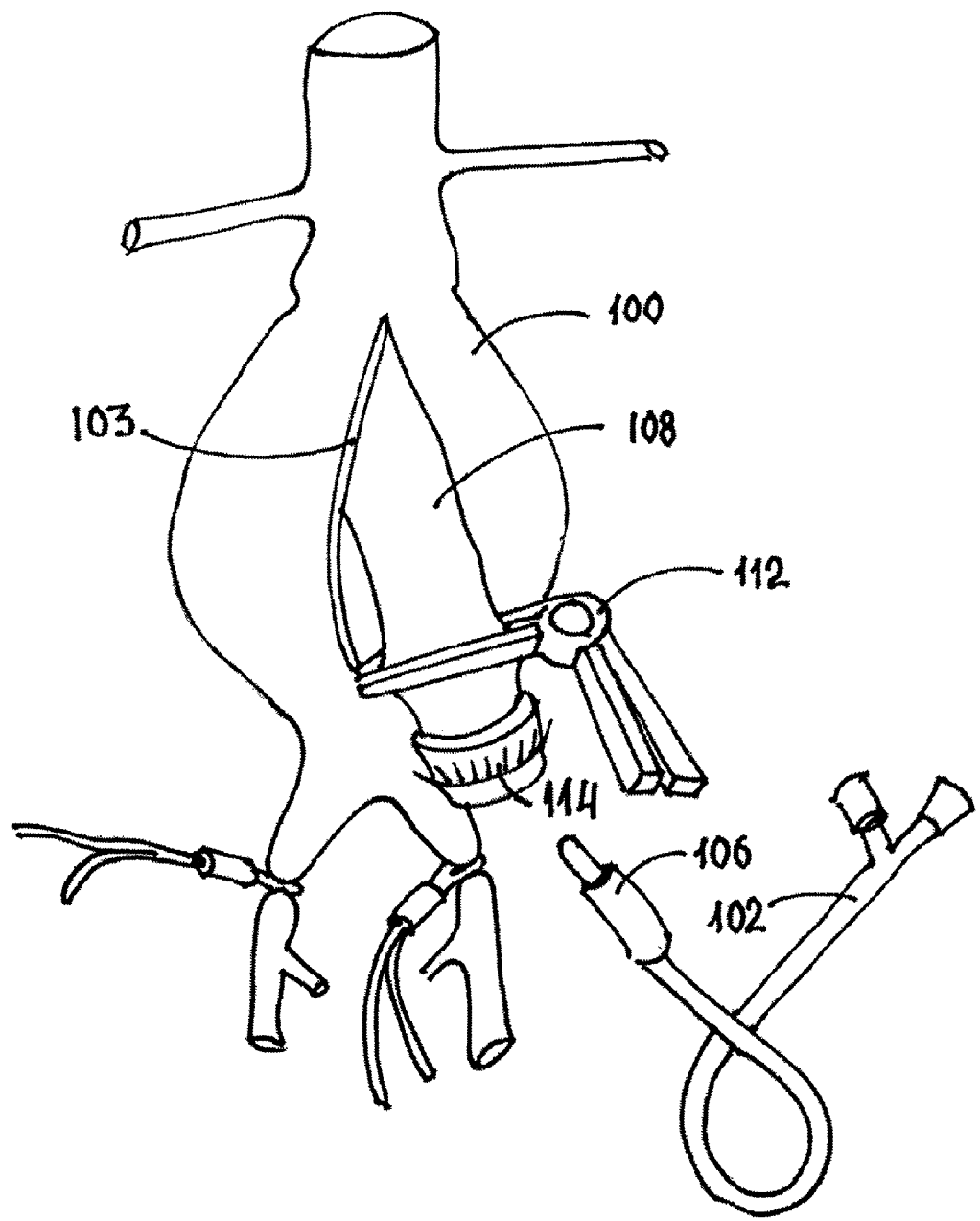
Figure 11:
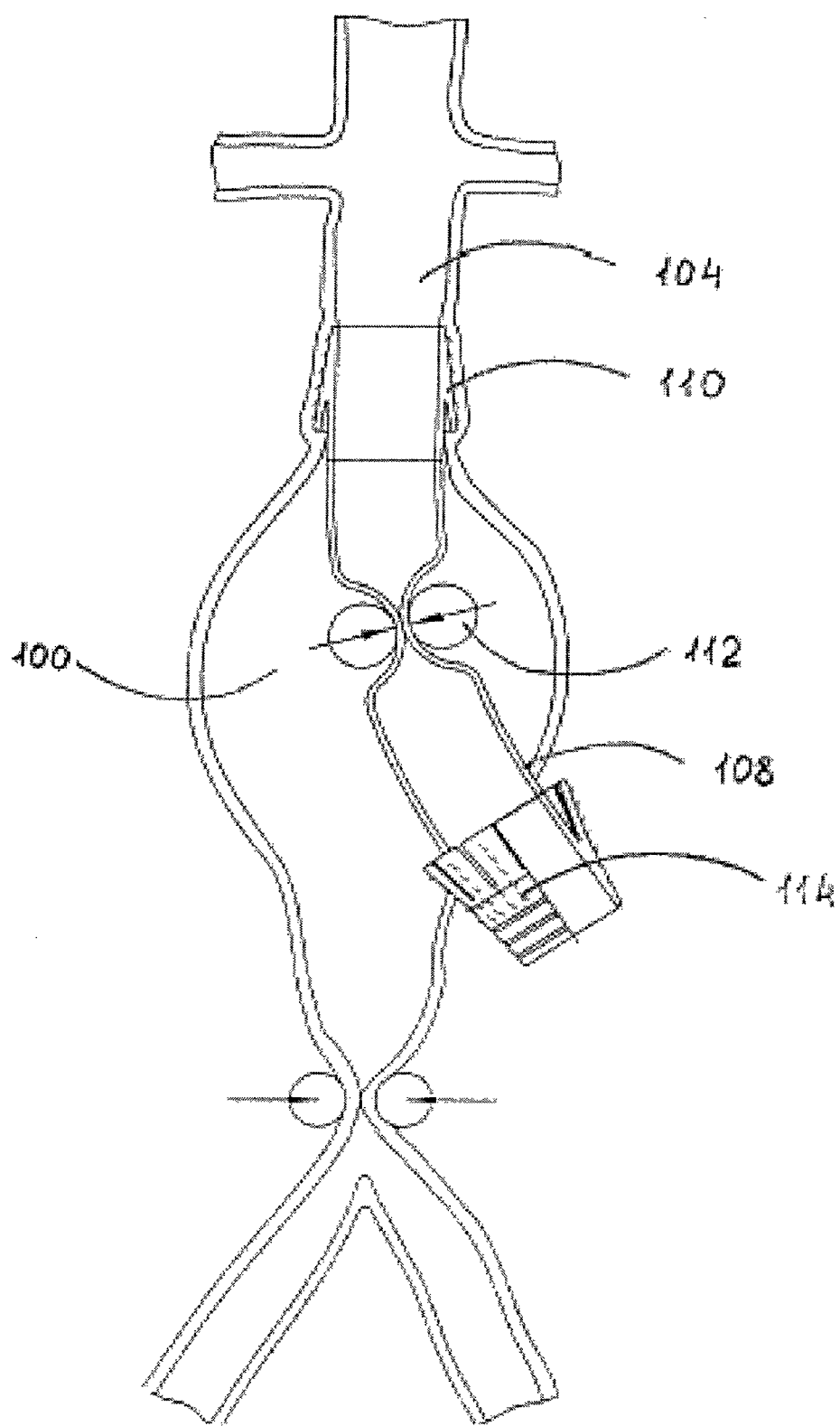
Figure 12:
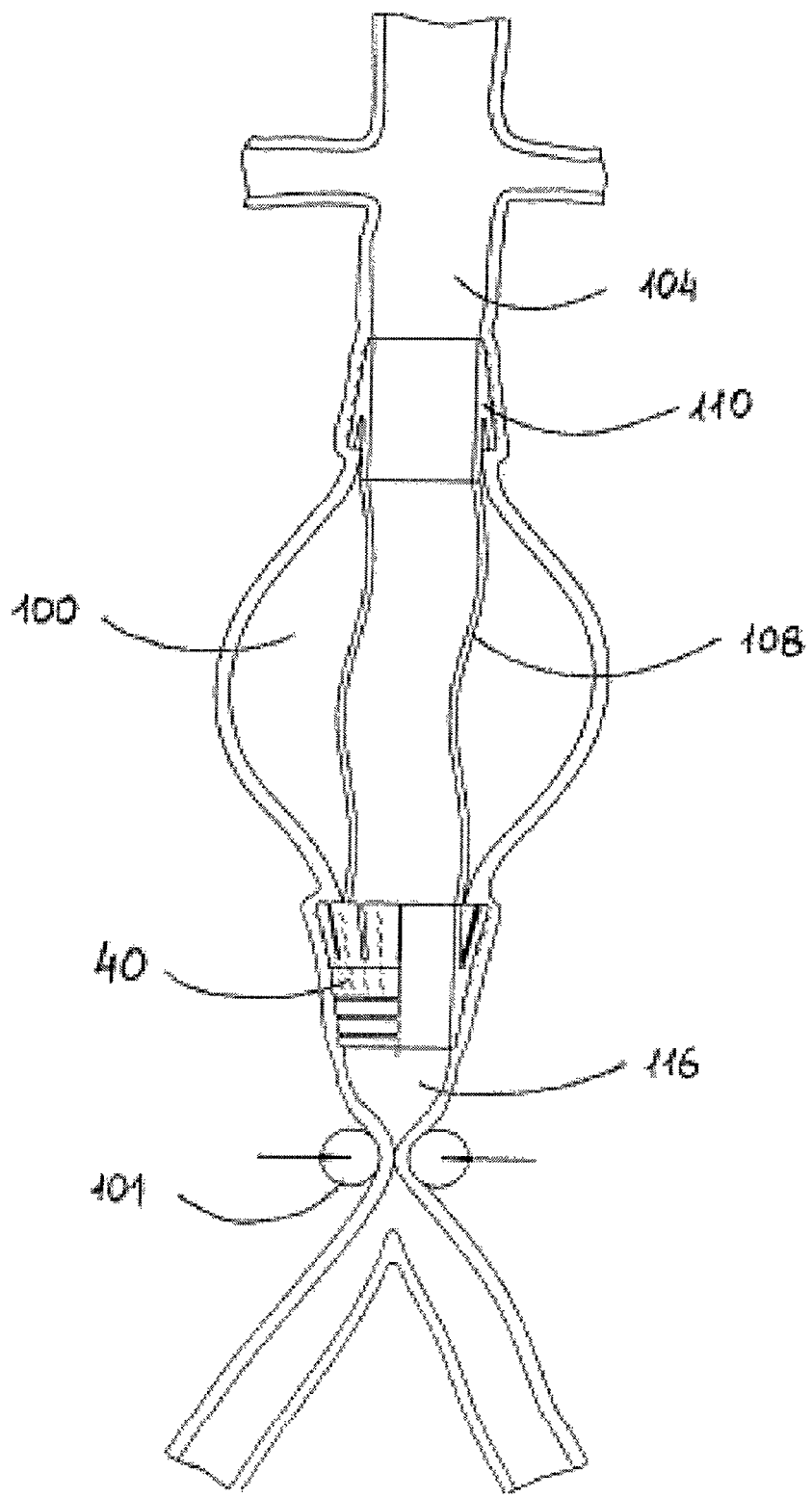

Reference is now made to FIGS. 8-13 illustrating stages of graft installation in a vessel with aneurysm using a delivery catheter in accordance with another preferred embodiment of the present invention. In cases the aneurysm is in the upper portion of the aorta, for example, and there is still a healthy portion before the bifurcation of the vessel, one can use a straight graft such as the graft shown herein. According to angiographic results, the graft approximate measures can be taken and a suitable graft can be prepared. Than, midline laporotomy is performed so as to approach the infrarenal abdominal aorta and exposing the aneurysm's necks. Vascular clamps are being positioned. FIG. 8 illustrates an aorta having an aneurysm 100 in the upper portion. The procedure is similar to the procedure described already herein, puncturing the side wall of aneurysm 100 by a catheter 102, positioning it in the vessel's healthy neck 104 and inflating a balloon 106 so as to firmly maintain catheter 102 for graft guidance. While the aneurysm is being punctured by the delivery device, the blood in the proximal neck can be stopped even with a finger due to the very short act. Vascular clamping is performed in the distal side of aneurysm 100 by vascular clamp 101 and in the proximal portion, by balloon 106. The size of the graft is being evaluated again and fixed to suit the size of aneurysm. Then, an incision in the side wall of the aneurysm is performed as well as suctioning the blood residuals so as to allow a graft 108 to be mounted onto delivery catheter 102 (incision 103 is shown in FIG. 10). Similarly to bifurcated graft 10, graft 108 is provided with docking heads. A first docking head 110 is provided in the distal end of graft 108 that is being guided onto catheter 102. Docking head 110 is advanced into neck 104 and then pulled back so as to nail the flexible barbs into the wall of the proximal neck.

Figure 13:
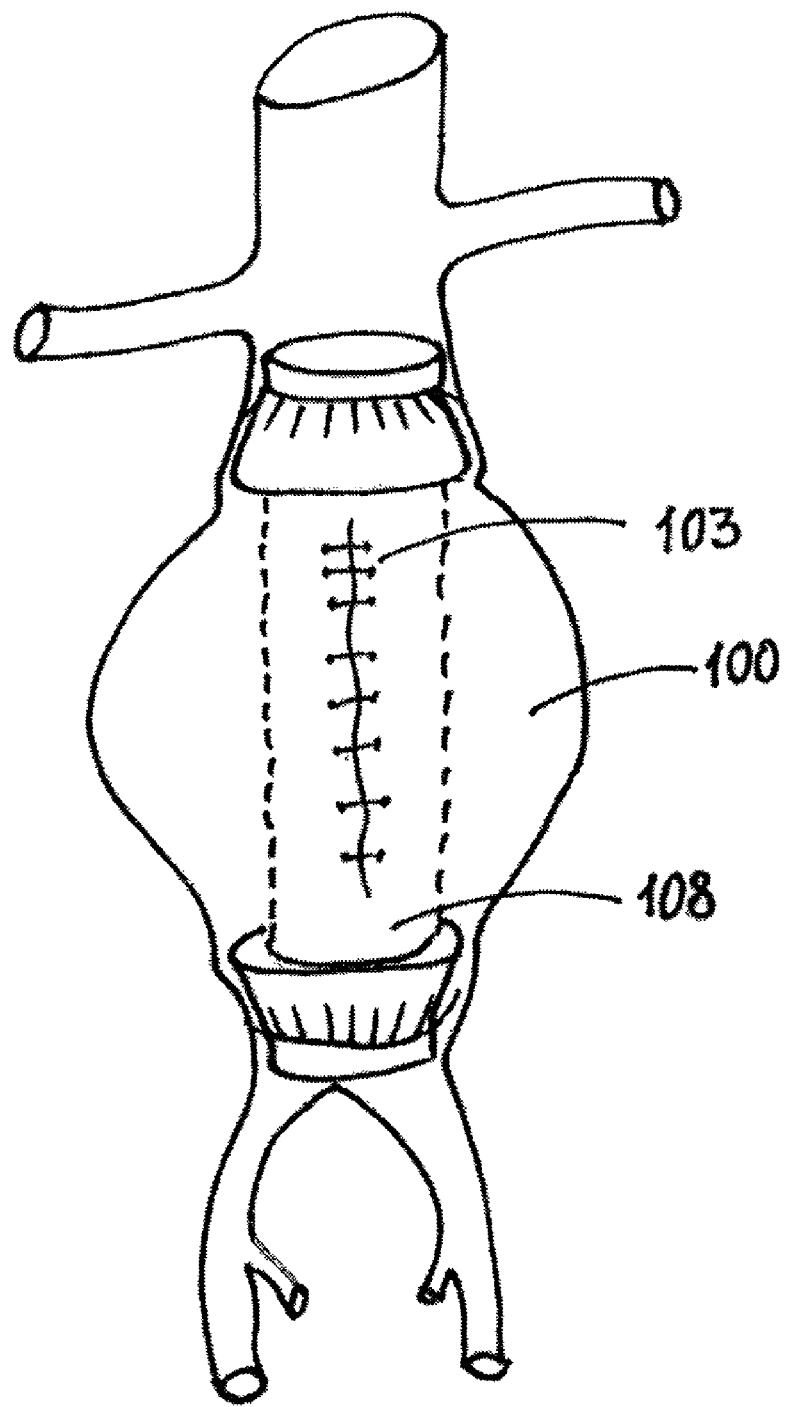

After the proximal end of graft 108 is firmly secured within neck 104, balloon 106 is slightly deflated so as to allow its withdrawal through graft 108 as shown in FIGS. 9 and 10. Catheter 102 is withdrawn and a clip 112 is clipped onto graft 102 so as to stop blood flow. The distal portion of graft 108 is free to be docked into the distal neck of the vessel. Docking head 114 is inserted into the aneurysm and positioned within the distal healthy neck 116. Again, due to the elastic barbs provided on docking head 114, its connection to the neck is very quick and firm by advancing the docking head forward and then slightly withdrawing it backwardly so that the barbs are nailed into the neck. Vascular clamp 101 can be removed so as to restore blood flow to the portions of the body that receives blood from the vessel. FIG. 13 shows the vessel after incision 103 is sutured. This procedure can be performed also using another delivery device other then a delivery catheter as will be shown herein after.

Figure 14:
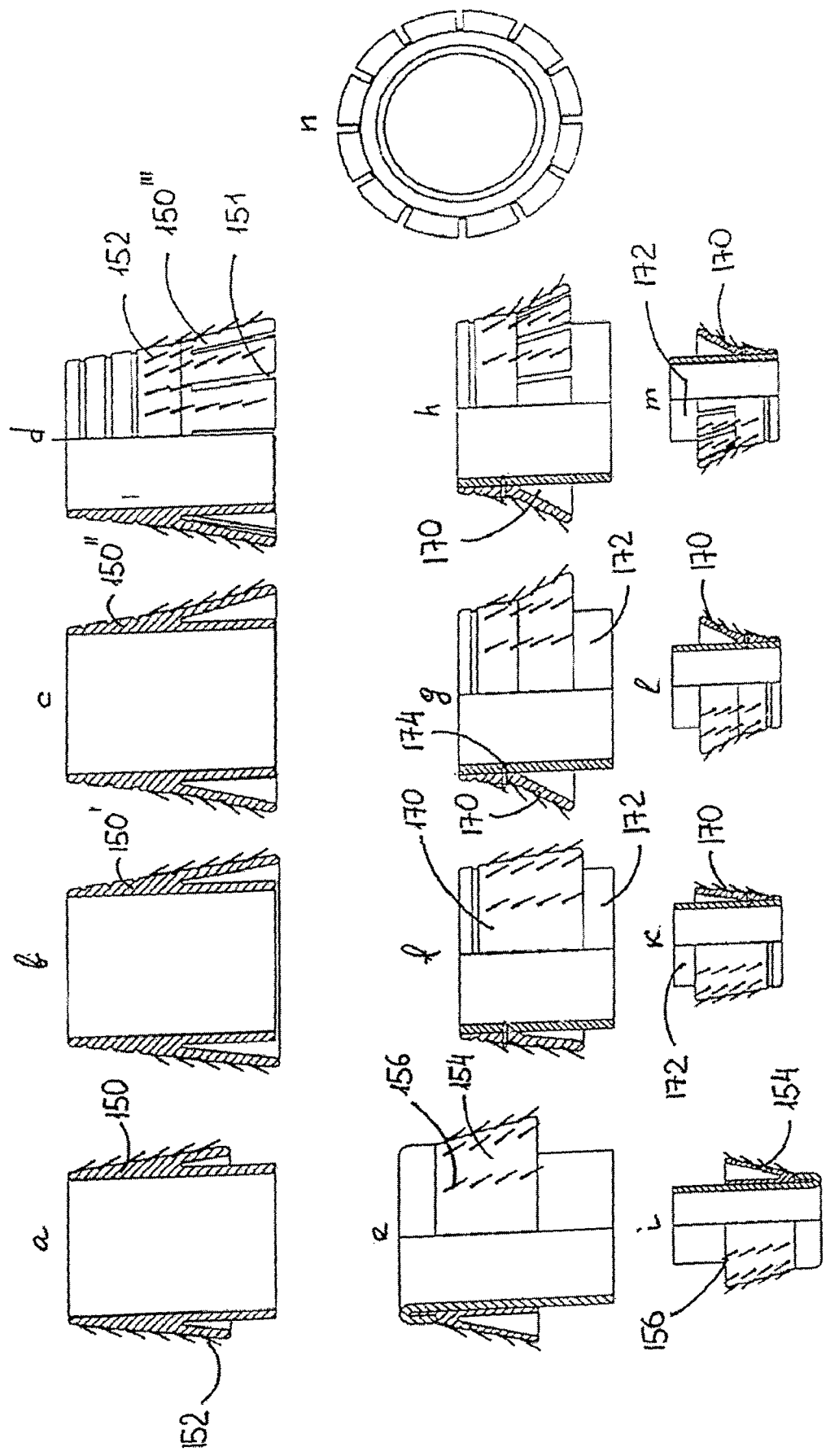
FIGS. 14a-n illustrate views of various configurations of docking heads in accordance with several preferred embodiments of the present invention.

Reference is now made to FIG. 14 *a-n* illustrating views of various configurations of docking heads in accordance with several preferred embodiments of the present invention. The docking heads shown herein are adapted to connect the graft within the vessel in a suture-less manner so as to establish a firm and secured connection as well as a connection that fully seals the vessel so as to ensure that there is no leak of blood through the connections. Generally, the docking heads are hollow thin-walled elastic truncated cones that are mounted onto the end of the graft. The small diameter end of the cone is fitted to the external diameter of the vessel and the bigger diameter surpasses it for about 1-10 mm. The cones can be concaved as shown in embodiments g, h, l, and m so as to facilitate its insertion into the aneurysm's neck; however, they can be straight as in a-f or convex. The cones are provided preferably with elastic barbs on the cones external surface. The barbs are inclined relative to the cone and are directed to the direction of the graft's body. It is preferable that the length of the barbs will not exceed the thickness of a wall of the vessel so as to prevent puncturing the vessel.

In FIGS. 14 *a-d*, the docking head is a conical structure 150, 150', 150" and 150'", respectively. The conical structure can be of relatively short length (150) or longer (150"), depending on the length of the healthy portion of the neck in which it has to be coupled. The conical structure is provided with a plurality of barbs 152 that are adapted to nail into the neck at the edges of the aneurysm. Barbs 152 are preferably flexible. It is shown in embodiment d that the cone is provided with slits 151 that enables the cone to curtail from its outer diameter when it is introduced into the neck so as to facilitate its insertion. The slits can be of about 0.3-0.6 cm.

FIG. 14 *e* and illustrate conical structures 154 that are produced by outwardly everting the end of the graft's body so that the truncated cone is an extension of the graft. The truncated cone is provided with bards 156.

Modular docking heads are shown in FIGS. 14 *f-h* and 14*k-n*. The modularity of the docking head provides the device with versatility so that the surgeon can decide in any stage of the operation which docking head to use. A truncated cone 170 is mounted on the edge of graft 172 and is connected to it by a connector 174. The advantage in these types of docking heads is that the type can be chosen of a plurality of different types even during operation when the surgeon can adapt the right cone that suits the inner structure of the particular vessel. The length of the cone as well as its angle can be different. The surgeon can prepare in advance an elongated graft having a stable docking head in the graft's proximal end and a modular docking head that is slidably provided in the distal portion of the graft. After the surgeon docks the proximal docking head of the graft in the proximal neck, he may measure in real time the actual length of the graft and stabilize the slidable distal docking head in a suitable place while the residual graft can be cut. In any of the embodiments, plurality of barbs is provided on each one of the cones.

Figure 15:
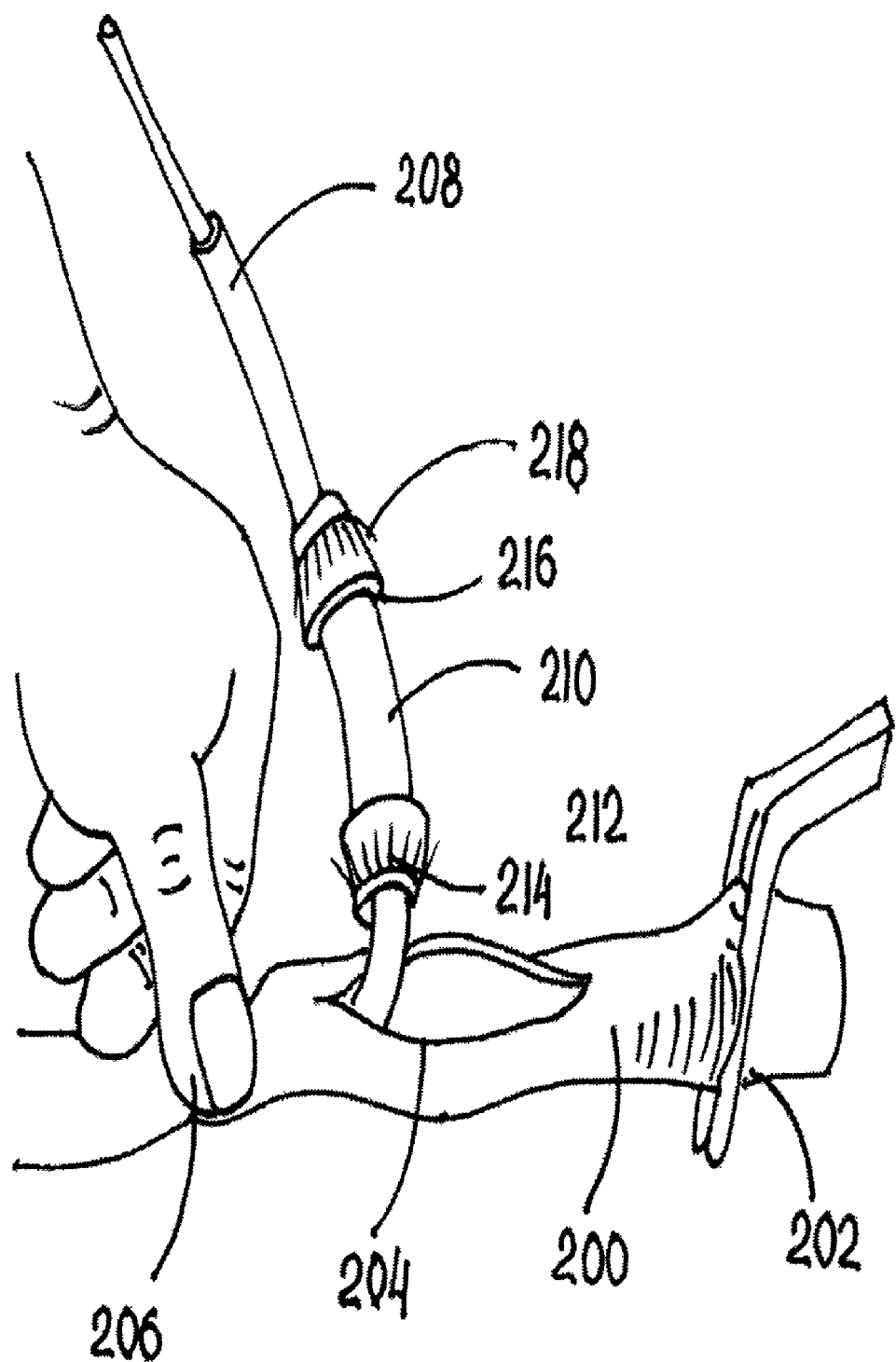
FIG. 15 illustrates an isometric view of graft insertion into aorta guided by a delivery catheter tube in accordance with another preferred embodiment of the present invention.

Reference is now made to FIG. 15 illustrating an isometric view of graft insertion into aorta guided by a delivery device in accordance with another preferred embodiment of the present invention. Since the procedure in accordance with the present invention is very quick and there is a desired to stop the blood flow to the organs for a minimum amount of time, the proximal portion of a vessel 200 can be clipped with a vascular clamp 202 so as to stop the blood flow to the aneurysm area. An incision 204 is performed in the aneurysm area while a finger 206 blocks the proximal side of the vessel. Alternatively, another vascular clamp can be used in order to block the proximal side. A guide 208 is inserted into the proximal portion of vessel 200 while a graft 210 is mounted on guide 208. After the positioning of the guide in the healthy neck in the proximal side of the vessel, the proximal side of graft 210 is placed within the corresponding neck while pulled slightly outwardly in order to nail barbs 212 of docking head 214 in the distal neck. Guide 208 is then removed and the proximal portion of graft 210 is inserted within the vessel. Docking head 216 that is connected to the distal side of graft 210 is placed within the distal portion of the healthy vessel's neck while pulled slightly outwardly in order to nail bards 218. The blood flow then can be restored.

Eliminating the need to suture the graft to the proximal and distal portions of the vessel enables a rapid procedure and offers the use of many other delivery devices so as to implant the graft into the vessel.

Figure 16:
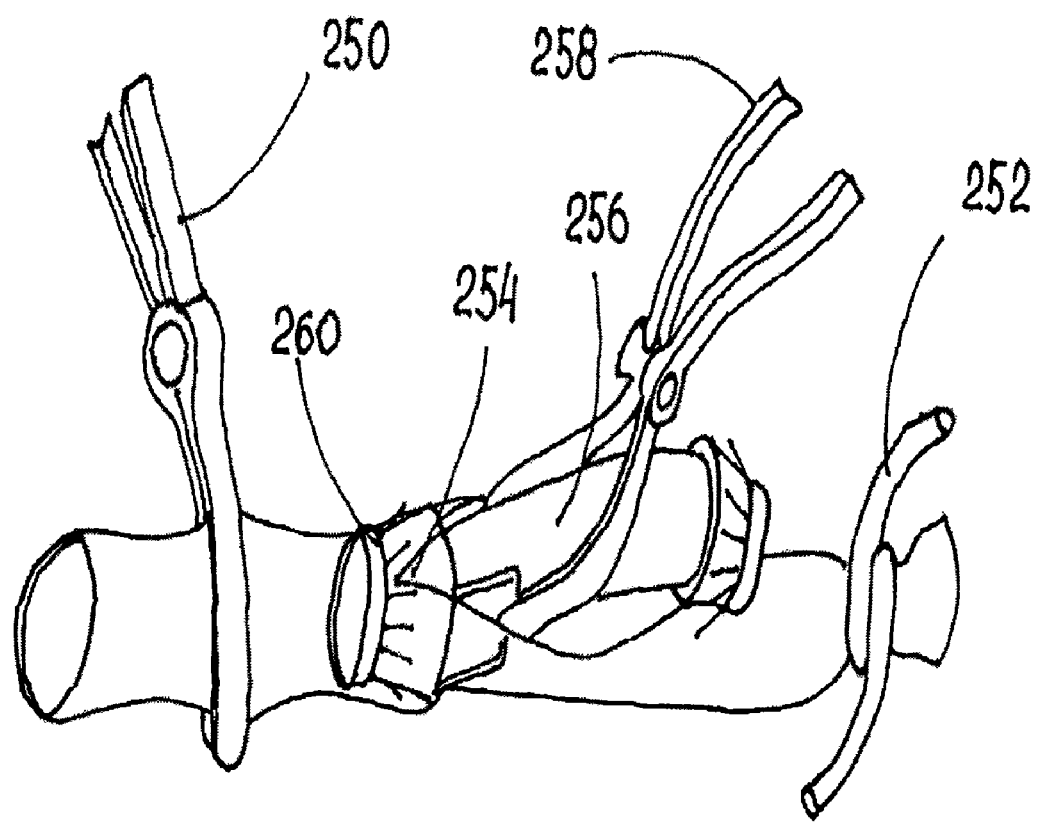
FIG. 16 illustrates an isometric view of graft positioning using forceps adapted for outer grasping in accordance with a preferred embodiment of the present invention.

Reference is now made to FIG. 16 illustrating an isometric view of graft positioning using forceps in accordance with a preferred embodiment of the present invention. Similarly to the previous procedure, blood is stopped using vascular clamp 250. A clip 252 is also put on the distal side of the vessel. An incision 254 is performed in the aneurysm and a graft 256 is positioned within the proximal portion of the vessel using a forceps 258 with jaws. Graft 256 is held and positioned within the vessel using forceps 258 having its jaws inserted between docking head 260 conic structure and the graft itself so as to gain control on the positioning of the graft's proximal side. The proximal docking head 260 is placed and nailed to the vessel's proximal portion. Forceps 258 are removed from the proximal portion of the vessel and then can be used in order to connect the distal side of the graft.

Figure 17:
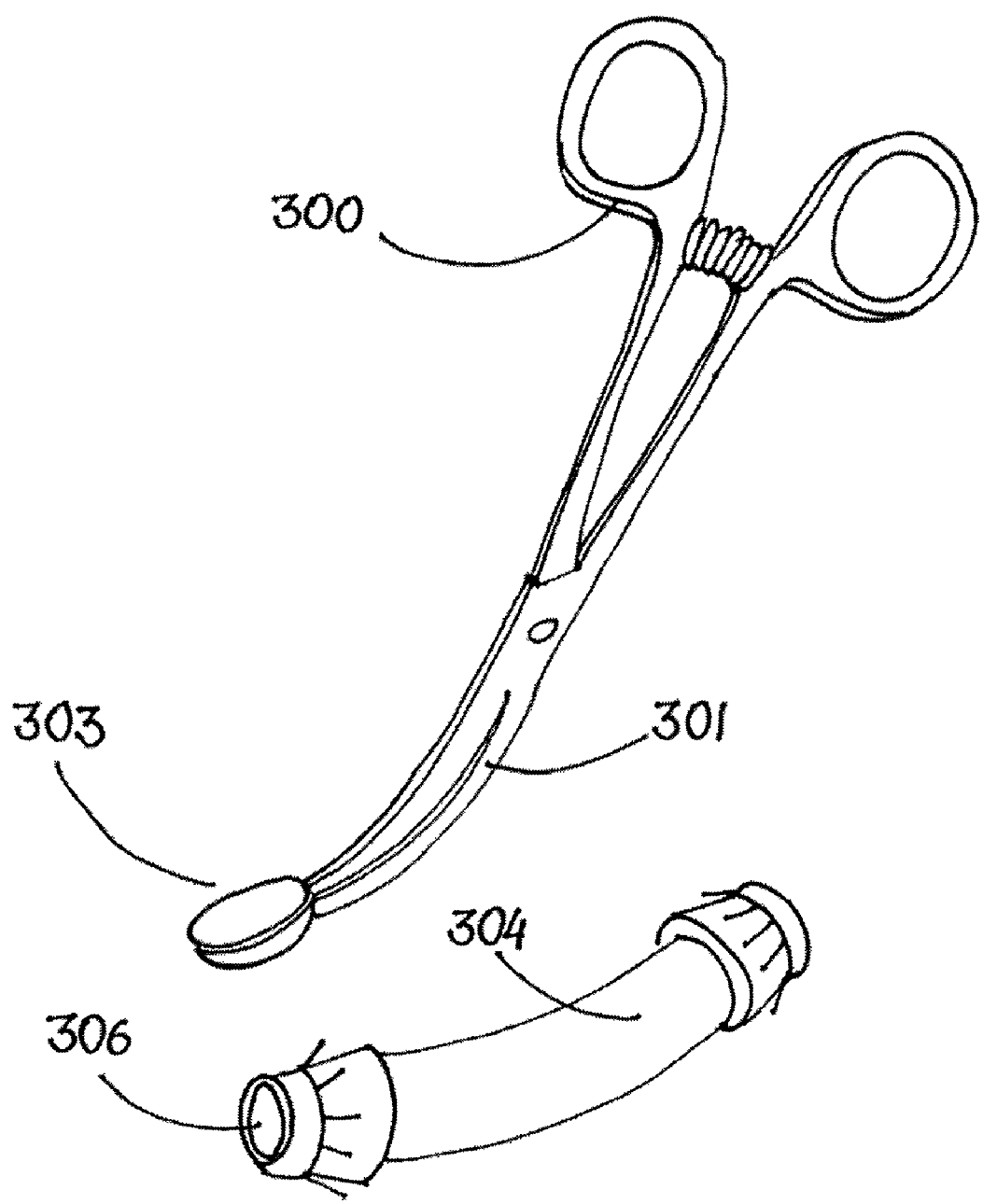
FIG. 17 illustrates an isometric view of forceps adapted for inner catching of a graft fastener in accordance with another preferred embodiment of the present invention.

Reference is now made to FIG. 17 illustrating an isometric view of forceps adapted for inner catching of a graft in accordance with another preferred embodiment of the present invention. Forceps 300 are designed with jaws 302 that are adapted to guide a graft 304 into the vessel. Jaws 302 have an elongated and curved body 301 and rounded and pointed head 303 at its edge. Elongated and curved body 301 is adapted to be threaded within graft 304 and rounded and pointed head 303 is designed to accord the inner diameter and shape of the edge 306 of graft 304.

Figure 18:
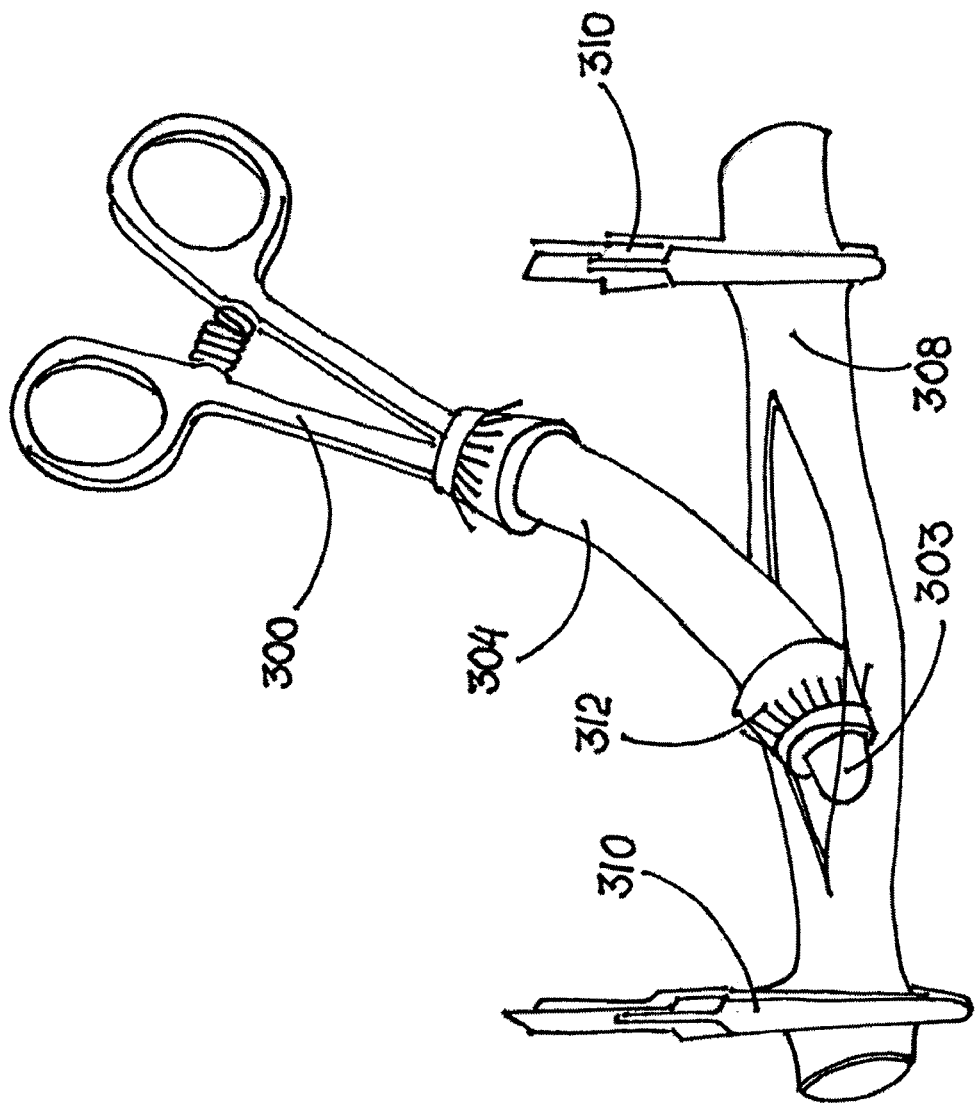
FIG. 18 illustrates the insertion of the graft to the vessel using forceps shown in FIG. 17.

Reference is now made to FIG. 18 illustrating the insertion of the graft to the vessel using forceps shown in FIG. 17. Vessel 308 is clipped by clips 310 as described herein before, proximally of an aneurysm and distally of it. An incision is made so as to insert the graft. Graft 304 is mounted onto jaws 302 while rounded head 303 partially protrudes beyond the graft, guiding the way to the proximal portion of the vessel 308. Using forceps 300, the surgeon directs docking head 312 into the healthy proximal portion of vessel 308 and couples it in the method described herein before. Then, the distal side can be coupled in the same manner.

It should be clear that the description of the embodiments and attached Figures set forth in this specification serves only for a better understanding of the invention, without limiting its scope as covered by the following Claims.

It should also be clear that a person skilled in the art, after reading the present specification can make adjustments or amendments to the attached Figures and above described embodiments that would still be covered by the following Claims.

The invention claimed is:

1. An anastomosis method for treating a vessel having an aneurysmal or occlusive disease edged by a proximal portion and a distal portion, wherein the portions are suitable for anastomosis, said method comprising:
   preparing a vascular graft to a length and a diameter corresponding to dimensions of the proximal and distal portions of the vessel, wherein said vascular graft has at least one distal end and a proximal end;
   choosing during the operation which docking head suits an inner dimension of the vessel being treated based upon a size of the inner dimensions;
   connecting at least two chosen docking heads, wherein each docking head comprises thin-walled hollow truncated head having a passage that fits an outer diameter of the vascular graft wherein said hollow truncated head and a portion of each docking head is provided with a plurality of outwardly pointing and inclined barbs and the barbed portion is non-expandable, wherein a first docking head is connected to said proximal end and at least one second docking head is connected to said distal end;
   providing a delivery tool;
   stopping flow of blood in the vessel in the proximal portion and the distal portion;
   performing an incision at a diseased portion of the vessel between the proximal portion and the distal portion and cleaning it;
   inserting through said incision said proximal end to the proximal portion manually or by a delivery tool;
   slightly pulling backwardly said proximal end so as to dock said first docking head in the proximal portion;
   inserting through said incision said distal end to at least on said distal portion manually or by a delivery tool;
   restoring the fluid flow; and
   suturing the incision.

2. The method as claimed in claim 1, wherein the vascular graft is tubular.

3. The method as claimed in claim 1, wherein the vascular graft comprises at least one branch.

4. The method as claimed in claim 1, further comprising slightly pulling backwardly the distal end so as to dock said at least one second docking head in the distal portion.

5. The method as claimed in claim 1, wherein said delivery tool is a tubular catheter comprises a removable wire such as a mandrel capable of being concealed, wherein the wire has a sharp tip and wherein the wire prevents the catheter from sliding backwardly, and an inflatable balloon at its proximal end, wherein said method further comprising:
   mounting said vascular graft over said tubular catheter;
   perforating the blood vessel by said sharp tip;
   concealing said sharp tip;
   advancing said tubular catheter to the proximal portion;
   inflating said balloon so as to fix said tubular catheter in the proximal portion and stop the fluid flow in one portion;
   stopping the fluid flow in at least one of said distal portion;
   performing an incision in the vessel wall over the body of the tubular catheter;
   removing said wire;
   guiding said proximal end of the graft to the proximal portion; and
   deflating said balloon and removing said tubular catheter through said vascular graft.

6. The method as claimed in claim 1, wherein the barbs are flexible and are laterally inclined with regard to said hollow truncated portion, and point opposite a direction said docking head travels to guide the vascular graft so as to allow their anchoring into the vessel wall then moving in a backward direction to prevent further backward movement.

7. The method as claimed in claim 1, wherein said thin-walled hollow truncated head has a concave, convex or straight profile that is capable of conforming to a vessel's profile when the docking head is coupled to a vessel wall.

8. The method as claimed in claim 1, wherein a smaller diameter end of the substantially conical thin-walled hollow truncated portion is sized to fit an external diameter of the vessel, and wherein a larger diameter end of the substantially conical thin-walled hollow truncated portion is sized approximately 1-10 mm larger than the external diameter of the vessel.

9. The method as claimed in claim 1, wherein said hollow truncated head includes a fixed shape and size portion where the barbs are provided.

* * * * *